(12) United States Patent
Bornzin et al.

(10) Patent No.: US 7,925,348 B1
(45) Date of Patent: Apr. 12, 2011

(54) EXTRA-CARDIAC IMPEDANCE BASED HEMODYNAMIC ASSESSMENT METHOD AND SYSTEM

(75) Inventors: Gene A. Bornzin, Simi Valley, CA (US); Xiaoyi Min, Thousand Oaks, CA (US)

(73) Assignee: Pacesetter, Inc., Sylmar, CA (US)

( * ) Notice: Subject to any disclaimer, the term of this patent is extended or adjusted under 35 U.S.C. 154(b) by 0 days.

(21) Appl. No.: 12/694,078

(22) Filed: Jan. 26, 2010

(51) Int. Cl.
*A61N 1/00* (2006.01)
(52) U.S. Cl. .......................................................... 607/23
(58) Field of Classification Search .................. 607/23
See application file for complete search history.

(56) References Cited

U.S. PATENT DOCUMENTS

| | | | |
|---|---|---|---|
| 5,078,133 A | 1/1992 | Heinz et al. | |
| 5,170,785 A | 12/1992 | Heinz et al. | |
| 6,986,741 B2 | 1/2006 | Poliac et al. | |
| 7,149,573 B2 * | 12/2006 | Wang | 600/547 |
| 2005/0070986 A1 | 3/2005 | Tockman et al. | |
| 2009/0099614 A1 | 4/2009 | Holmstrom et al. | |
| 2011/0004264 A1 * | 1/2011 | Siejko et al. | 607/28 |

FOREIGN PATENT DOCUMENTS

WO 2007100276 A1 9/2007

OTHER PUBLICATIONS

Patterson, R.P., "Fundamentals of Impedance Cardiography," IEEE Engineering and Biology Magazine. Mar. 1989:35-38.

* cited by examiner

*Primary Examiner* — George Manuel

(57) ABSTRACT

A medical device is provided that comprises a lead assembly configured to be at least partially located proximate to the heart. The lead assembly includes an extra-cardiac (EC) electrode to be positioned proximate to at least one of a superior vena cava (SVC) and a left ventricle (LV) of a heart. The lead assembly includes a subcutaneous remote-cardiac (RC) electrode configured to be located remote from the heart such that at least a portion of the greater vessels are interposed between the RC electrode and the EC electrode to establish an extra-cardiac impedance (ECI) vector. The processor module measures extra-cardiac impedance along the ECI vector to obtain ECI measurements. The processor module assesses a hemodynamic performance based on the ECI measurements.

20 Claims, 17 Drawing Sheets

EXTRA-CARDIAC IMPEDANCE BASED HEMODYNAMIC ASSESSMENT METHOD AND SYSTEM

FIELD OF THE INVENTION

Embodiments of the present invention generally relate to hemodynamic assessment, and more particularly to methods and devices that utilize extra-cardiac impedance measurements to derive cardiac output.

BACKGROUND OF THE INVENTION

Implantable medical devices (IMD) are well known in the art. The IMD may take the form of implantable defibrillators or cardioverters which treat accelerated rhythms of the heart such as fibrillation. The IMD may also take the form of implantable pacemakers which maintain the heart rate above a prescribed limit, such as, for example, to treat a bradycardia. Implantable medical devices may also incorporate more than one of a pacemaker, a cardioverter and a defibrillator. Defibrillators may include "shock only" functionality or, in addition to shocking functionality, a defibrillator may be capable of providing cardiac resynchronization therapy (CRT) functionality. Shock only devices and CRT devices are typically coupled to different lead configurations. As a further example, the IMD may be an implantable monitoring device, such as the Confirm™ device offered by St. Jude Medical.

An IMD is comprised of three major components. One component, at least in stimulation type IMDs, is a pulse generator which generates the stimulation pulses and includes the electronic circuitry and the power cell or battery. The second component, at least in stimulation type IMDs, is the lead, or leads, which electrically couple the IMD to the heart. IMDs deliver stimulation pulses to the heart to cause the stimulated heart chamber to contract when the patient's own intrinsic rhythm fails. The third component is a sensor and detection module that monitors a heart for cardiac signals and analyzes the cardiac signals to identify normal sinus rhythm, arrhythmias and the like. To this end, IMDs include sensing circuits that sense cardiac activity for the detection of intrinsic cardiac events such as intrinsic atrial events (P-waves) and intrinsic ventricular events (R-waves). By monitoring P-waves and/or R-waves, the IMD circuits are able to determine the intrinsic rhythm of the heart and provide stimulation pulses that force atrial and/or ventricular depolarizations at appropriate times in the cardiac cycle when required to help stabilize the electrical rhythm of the heart.

IMDs detect various arrhythmias such as atrial fibrillation (AF), atrial flutter (A-flutter), and atrial tachycardia (AT) (hereafter collectively atrial arrhythmias). Arrhythmias are detected based on one or more of ventricular rate, rate stability, and the morphology of the cardiac signal. However, conventional algorithms for detecting arrhythmias experience certain limitations. For example, conventional AF detection algorithms that are based on rate stability may become confounded when an atrial tachyarrhythmia drives a ventricle at a high, but very stable rate. When a patient experiences atrial tachyarrhythmia having a stable rate, the AF detection algorithm may classify the events merely as high rate normal sinus events. Thus, the AF detection algorithm may not declare the events to be pathologic (non-physiologic) and may not deliver a therapy. Further, conventional algorithms may not correctly classify atrial fibrillation that exhibits rate dependent changes in the QRS complex. When a patient experiences atrial tachyarrhythmia having rate dependent changes in the QRS complex, the morphology detection algorithm may classify the events merely as physiologic events and thus, may not declare the events to be pathologic.

At least certain limitations of conventional detection algorithms extend, in part, from the fact that the algorithms analyze intra-cardiac electrogram (IEGM) signals from various combinations of electrodes within and surrounding the heart. IEGM signals are a direct indicator of the electrical activity within the tissue of the heart. While heart tissue electrical activity is a good indicator of heart behavior, the electrical activity is not a direct indicator of the resultant actual "mechanical" output of the heart. The mechanical output of the heart constitutes the actual cardiac output (CO) of the heart. Cardiac output represents a volume of blood that is ejected from the heart over a period of time. For example, the cardiac output may be quantified in terms of the stroke volume (ml/heart beat) times the heart rate (beats/minute). While IEGM signals are a good approximation of cardiac output, IEGM signals are not a direct indicator of hemodynamic performance.

Heretofore, various intra-cardiac indicators (ICI) have been proposed for monitoring cardiac activity, such as heart sounds, blood pressure, and the like. It has also been proposed to monitor certain types of intra-cardiac impedance (within the heart) to derive hemodynamic performance. Intra-cardiac impedance represents impedance that is measured between electrodes that are located within the heart (intra-cardiac electrodes). For example, the intra-cardiac electrodes may be located within the right atrium and the right ventricle with the intra-cardiac impedance measured therebetween. The intra-cardiac electrodes define an intra-cardiac impedance vector that extends through one or both of the atrium and ventricle. The entire intra-cardiac impedance vector or at least a substantially majority of the intra-cardiac impedance vector lies within, and extends through, the blood pool in the chambers of the heart.

Intra-cardiac impedance exhibits a high value when the associated heart chamber(s) are in a systole state. The intra-cardiac impedance exhibits a low value when the associated heart chamber(s) are in a diastole state. As the corresponding heart chambers transition between systole and diastole, the impedance waveform moves between peaks and valleys. The intra-cardiac impedance waveform has not proven to be a good indicator of stroke volume or cardiac output. One limitation of the intra-cardiac impedance waveform arose from the fact that the intra-cardiac impedance vector extends through multiple chambers of the heart. Thus, each measurement of intra-cardiac impedance includes components from individual chambers of the heart, not the overall cooperative effect of all of the heart chambers.

A need remains for an improved method and system for assessing hemodynamic behavior of the heart through an indicator that is direct associated with cardiac output.

Further, not all patients respond equally to implantation of an IMD. The type of IMD, therapy, type and combination of leads and lead placement all impact the effectiveness of the IMD. For example, certain patients who receive pacemakers or CRT devices may respond well, while other patients may not experience a significant improvement in physiologic behavior. During implantation, once the lead(s) are installed the leads are connected to an external pacing system analyzer (PSA). The PSA delivers a desired therapy and the response of the heart is monitored to determine the effectiveness of the lead placement and therapy configuration. The response is measured through IEGM signals or the EKG signals. When a desired response is not achieved, the lead(s) may be replaced or moved, and the timing, voltage and polarity of the therapy may be changed in an effort to improve capture and overall effectiveness. This process is repeated until the IEGM or EKG signals indicate the best result. However, the IEGM and EKG signals are indicators of heart electrical activity, not cardiac output.

A need remains for an improved method and system for assessing and improving cardiac output, during implantation, as well as the overall responsiveness of the patient to the IMD.

Moreover, patients are indicated to receive different types of IMDs based upon various criteria, including the patient's morphology and type of arrhythmia. Depending upon the type of arrhythmia, the patient may be indicated for a pacemaker, a CRT device or a shock only defibrillator. A patient having a low cardiac ejection fraction may receive a CRT device or a shock only defibrillator. When the patient exhibits low ejection fraction (EF) and has a narrow QRS complex (e.g., less than 130 to 140 ms), the patient will not be indicated for a CRT device (e.g. contra-indicated). The contra-indication occurs because cardiac resynchronization therapies have not been shown to have sufficient efficacy for patients with a narrow QRS complex. Thus these patients are not expected to realize a benefit from the CRT therapies available by a CRT device with a CRT lead. Thus, patients with a low EF and narrow QRS complex are indicated for shock only defibrillators and receive a shock only type of lead.

However, certain patients may benefit from CRT therapies even when the patient has a narrow QRS complex. Today, no convenient and cost effective mechanism exists to determine whether a patient, who has a narrow QRS complex, may still benefit from a CRT device. A need exists for a method and system that is capable of assessing intraoperatively, during implantation, whether CRT therapies would improve the cardiac output of an individual, notwithstanding a narrow QRS complex.

SUMMARY

In accordance with one embodiment, a medical device is provided that comprises a lead assembly configured to be at least partially located proximate to the heart. The lead assembly includes an extra-cardiac (EC) electrode to be positioned proximate to at least one of a superior vena cava (SVC) and a left ventricle (LV) of a heart. The lead assembly includes a subcutaneous remote-cardiac (RC) electrode configured to be located remote from the heart such that at least a portion of the greater vessels are interposed between the RC electrode and the EC electrode to establish an extra-cardiac impedance (ECI) vector. The processor module measures extra-cardiac impedance along the ECI vector to obtain ECI measurements. The processor module assesses a hemodynamic performance based on the ECI measurements.

Optionally, the EC electrode is located outside of the heart and in the SVC and the RC electrode is located in a left subclavical pocket of the patient. Optionally, the lead assembly forms a bipolar impedance configuration that measures impedance between the EC and RC electrodes. Optionally, the ECI vector passes through at least a portion of at least one of pulmonary arteries, pulmonary veins, brachiocephalic arteries and brachiocephalic veins, left carotid artery and left subclavian artery.

Optionally, the processor module analyzes parameters of the ECI measurements for current ECI values relative to ECI thresholds to determine whether sufficient hemodynamic performance exists. The hemodynamic performance includes one or more of cardiac output, systolic blood pressure, diastolic blood pressure, contractility, stroke volume, systolic time, Q-wave to onset of systole, and QRS to onset of systole.

The processor module obtains baseline ECI values from a baseline ECI measurement when normal hemodynamic performance is present. The processor module utilizes the baseline ECI values to analyze new ECI measurements to determine whether sufficient hemodynamic performance exists.

In accordance with an alternative embodiment, a method is provided for assessing hemodynamic stability. The method includes providing a lead assembly configured to be at least partially located proximate to the heart. The lead assembly includes an extra-cardiac (EC) electrode to be positioned proximate to at least one of a superior vena cava (SVC) and a left ventricle (LV) of a heart. The lead assembly includes a subcutaneous remote-cardiac (RC) electrode configured to be located remote from the heart such that at least a portion of the greater vessels are interposed between the RC electrode and the EC electrode. The method includes measuring extra-cardiac impedance along the ECI vector to obtain ECI measurements, and assessing hemodynamic performance based on the ECI measurements.

Optionally, the method may include locating the EC electrode outside of the heart and in the SVC and locating the RC electrode in a left subclavical pocket of the patient. The method analyzes parameters of the ECI measurements for current ECI values relative to ECI thresholds to determine whether sufficient cardiac output exists. The method obtains baseline ECI values from a baseline ECI measurement when normal hemodynamic performance is present, and utilizes the baseline ECI values to analyze new ECI measurements to determine whether sufficient hemodynamic performance exists. The method determines whether to apply a corrective therapy based on the ECI measurements.

In accordance with one embodiment, the method comprises collecting cardiac indicator (CI) signals, analyzing the CI signals utilizing an arrhythmia detection algorithm, declaring a CI based therapy when an arrhythmia episode is identified based on the CI signals, and suspending the CI based therapy when the ECI measurements indicate that sufficient hemodynamic performance exists.

In accordance with one embodiment, the method comprises collecting cardiac indicator (CI) signals, analyzing the CI signals utilizing an arrhythmia detection algorithm, declaring a non-therapy judgment when a rhythm episode is identified based on the CI signals, and over-ruling the non-therapy judgment and declaring an ECI based therapy when the ECI measurements indicate that insufficient hemodynamic performance exists.

In accordance with one embodiment, a system is provided for intra-operatively assessing cardiac output during implantation of an implantable medical device. The system comprises extra-cardiac (EC) electrodes to be located outside of a heart and positioned to define an extra-cardiac impedance (ECI) vector therebetween where at least a portion of the greater vessels are interposed between the EC electrodes along the ECI vector. At least one cardiac lead is positioned in contact with the heart, and an external device is connected to the EC and IC leads. The external device comprises a therapy control module to control and deliver an IC therapy to the heart through the IC lead, an impedance detection module to measure extra-cardiac impedance between the EC electrodes along the ECI vector to obtain ECI measurements, and an HDPassessment module to assess a hemodynamic performance based on the ECI measurements. The impedance detection module and hemodynamic performance assessment module repeating the ECI measurements and hemodynamic performance assessment after an adjustment of at least one of i) cardiac lead position, ii) cardiac lead configuration and iii) cardiac therapy. The external device includes a display to display hemodynamic performance associated with at least one of different cardiac lead positions and cardiac therapies.

The impedance detection module performs the measurement before delivering the cardiac therapy to obtain a baseline ECI measurement and after at least one of adjusting the cardiac lead position and delivering the cardiac therapy to obtain subsequent ECI measurements. The display compares cardiac outputs associated with the baseline and subsequent ECI measurements to identify a final cardiac lead position and final cardiac therapy. The HDP assessment module calculates successive cardiac outputs associated with different combinations of the cardiac lead position and the cardiac therapy, and identifies a final cardiac lead position and a final cardiac therapy that correspond to a selected one of the successive cardiac outputs.

In accordance with one embodiment, a method is provided for intra-operatively assessing hemodynamic performance during implantation of an implantable medical device. The method comprises providing extra-cardiac (EC) electrodes to be located outside of a heart and positioned to define an extra-cardiac impedance (ECI) vector therebetween where at least a portion of the greater vessels are interposed between the EC electrodes along the ECI vector. The method further comprises providing at least one cardiac lead to be positioned in contact with the heart, delivering cardiac therapy to the heart through the lead, measuring an extra-cardiac impedance between the EC electrodes along the ECI vector to obtain ECI measurements, assessing a hemodynamic performance based on the ECI measurements, adjusting at least one of i) a cardiac lead position, ii) cardiac lead configuration and iii) cardiac therapy, repeating the measuring and assessing; and identifying when at least one of i) the cardiac lead position, ii) the cardiac lead configuration and iii) the cardiac therapy improve hemodynamic performance based on the ECI measurements.

Optionally, the IC lead initially may represent a single chamber lead for an implantable defibrillator. The adjusting operation includes providing a CRT lead and a CRT therapy, and the identifying operation identifies whether the CRT lead and CRT therapy improve the cardiac output of the patient.

Optionally, the measuring operation is performed before the delivering operation to obtain a baseline ECI measurement and after at least one of the delivering and adjusting operations to obtain subsequent ECI measurements, the identifying operation including comparing hemodynamic performance associated with the baseline and subsequent ECI measurements to identify a final cardiac lead position, final cardiac lead configuration and final cardiac therapy.

DETAILED DESCRIPTION

Figure 1:
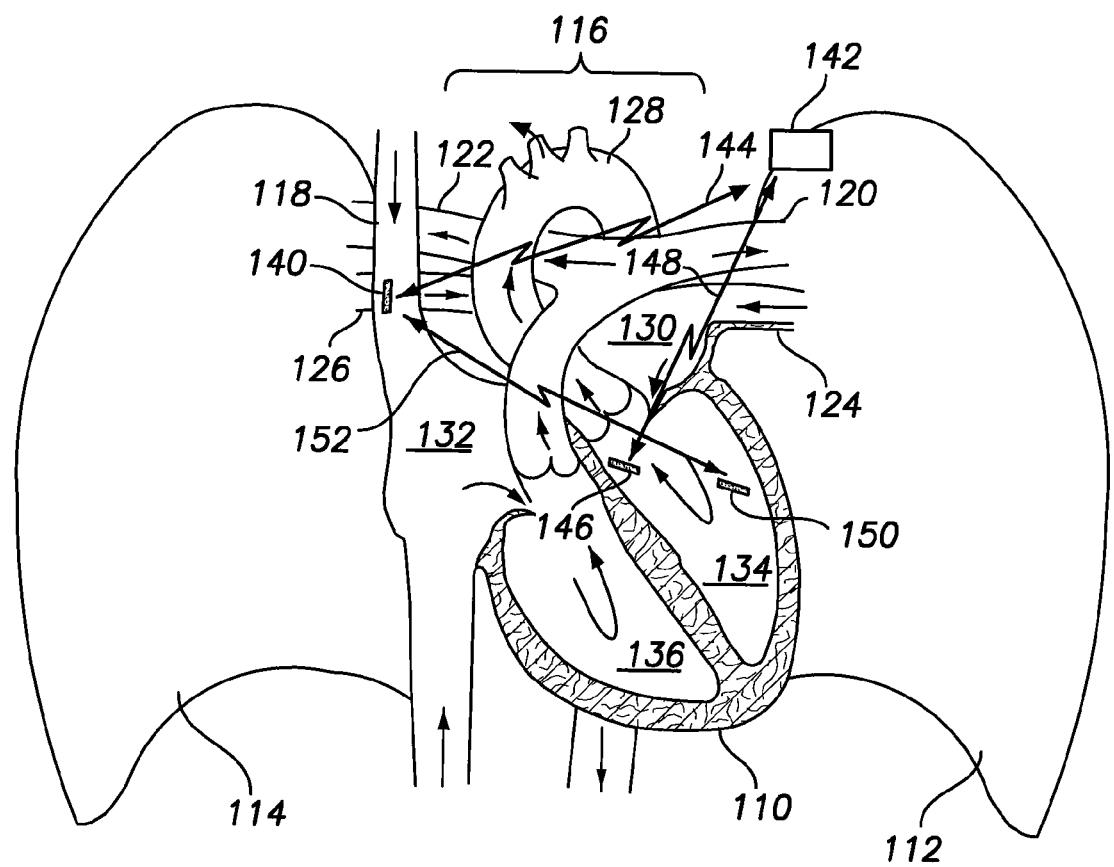
FIG. 1 illustrates a graphical representation of the upper torso of a human and illustrates various locations at which electrodes may be located outside of, but proximate to the heart, as well as at locations outside and remote from the heart in accordance with an embodiment.

In the following detailed description, reference is made to the accompanying drawings which form a part hereof, and in which are shown by way of illustration specific embodiments in which the present invention may be practiced. These embodiments, which are also referred to herein as "examples," are described in sufficient detail to enable those skilled in the art to practice the invention. It is to be understood that the embodiments may be combined or that other embodiments may be utilized, and that structural, logical, and electrical variations may be made without departing from the scope of the present invention. For example, embodiments may be used with a pacemaker, a cardioverter, a defibrillator, and the like. The following detailed description is, therefore, not to be taken in a limiting sense, and the scope of the present invention is defined by the appended claims and their equivalents. In this document, the terms "a" or "an" are used, as is common in patent documents, to include one or more than one. In this document, the term "or" is used to refer to a nonexclusive or, unless otherwise indicated.

In the context of this application, the term "impedance" refers to the relatively low frequency component of the impedance. The impedance is calculated as $z=u/i$, where u is the measured voltage and i is the applied excitation current.

The term "extra-cardiac impedance" is the impedance measured between electrodes that are located outside of the four chambers of the heart. Extra-cardiac impedance is measured along an impedance vector that extends through at least a portion of the greater vessels. The "extra-cardiac impedance" may be described as having an offset generally known as Zo. Zo is typically in the range of 30 to 100 ohms. Riding on top of the Zo is a signal that is modulated by respiration and ejection of blood into the greater vessels, $\Delta Z$. $\Delta Z$ decrease with each systolic ejection because blood injected into the great vessels has a lower impedance that the surrounding tissue. The great vessels are juxtapositioned between the measuring electrodes. In addition, the process of breathing modulates the signal as well because the electrodes move with each breath and because air is brought into the lungs raising the impedance with each inspiration. These relatively low frequency signals may be high pass filtered at about 0.7 to reject respiration which typically has frequency components of less than 0.2 hertz while the cardiac ejections have frequency components starting at about 1 hertz to about 14 hertz. The cardiac component of $\Delta Z$ is typically in the range about 0.5 to 4% of Zo and is in the range of 0.25 to 2 ohms.

The term "hemodynamic performance" is comprised of at least one of cardiac output, systolic blood pressure, diastolic blood pressure, contractility, stroke volume, systolic time, and Q-wave to onset of systole, QRS to onset of systole.

The term "cardiac pacing conditions" includes one or more of AV delay, V-V delay, stimulation rate, stimulating electrodes chosen for actuating pacing, and stimulation lead configuration.

The term "cardiac indicator" (CI) includes extra-cardiac and intra-cardiac indicators.

FIG. 1 illustrates a graphical representation of the upper torso of a human. FIG. 1 illustrates various locates at which electrodes may be located outside of, but proximate to the heart, as well as at locations outside and remote from the heart. Electrodes are positioned at these locations to measure extra-cardiac impedance. An IMD or an external PSA analyzer having an impedance plethysmograph then performs a hemodynamic performed assessment based on the impedance measurements. FIG. 1 illustrates the heart 110 between the left and right lungs 112 and 114. The direction of blood flow is noted by various arrows.

FIG. 1 also illustrates a portion of the greater vessels (generally denoted at 116) through which blood flows during entry to and exit from the heart 110. The greater vessels 116 generally include the superior vena cava (SVC) 118, the aorta 128, the pulmonary arteries 120 and 122, and the pulmonary veins 124 and 126. The greater vessels also include the left and right brachiocephalic arteries and veins, the left common carotid artery and left subclavian artery (not shown) which branch from the aorta 128. The heart 110 includes left and right atrium 130 and 132, and left and right ventricles 134 and 136.

In accordance with embodiments described herein, a lead assembly of one or more leads is provided having electrodes positioned outside of the heart 110 and located such that at least a portion of the greater vessels 116 are interposed between the electrodes. By way of example, an extra-cardiac (EC) electrode may be positioned at the superior vena cava 118, as denoted at EC electrode location 140. When an electrode is positioned at location 140, the electrode is outside of the heart 110, but proximate to the SVC 118, as well as proximate to the aorta 128, pulmonary veins 122 and pulmonary arteries 126. A second electrode may be located in a subcutaneous subclavical area, such as denoted at 142. Location 142 is remote from the heart 110 and, by way of example may correspond to the position at which an IMD is located.

The housing or case of the IMD may be configured to function as an electrode to, among other things, detect impedance and/or sense cardiac activity.

During intra-operative assessment the electrode 142 may be a surface electrode. This is because it may be desirable to make the impedance measurements prior to making the pocket for the IMD. Surface electrodes, such as ECG electrodes, may be used with one electrode to inject current and a neighboring electrode to detect the voltage. Alternatively, a single defibrillation patch electrode may be used to both inject current and measure the voltage. These techniques are used in impedance plethysmography. Alternatively, a large relatively low impedance electrode similar to the disposable electrodes used for defibrillation or as an electrocautery ground may be positioned preferably on the left thorax to establish an RC electrode. Alternatively, 142, the RC electrode, may be an electrode incorporated on the proximal portion of an introducer sheath. Introducer sheaths are used to facilitate venous access and to provide a conduit for lead placement.

Electrodes at locations 140 and 142 form an extra-cardiac impedance (ECI) vector 144 there between. The electrodes at locations 140 and 142 may be bipolar, mono-polar, tri-polar, or quadra-polar. The ECI vector 144 extends through a substantial portion of the aorta 128, as well as the pulmonary veins and arteries 122 and 126, and other portions of the greater vessels 116. The ECI vector 144 may be referred to as an aorta-centric ECI vector due to the correlation of the vector 144 and the aorta 128. Electrodes at locations 140 and 142 are both outside of the four chambers 130, 132, 134 and 136 of the heart 110.

Optionally, an electrode may be located within a coronary vein that passes along the heart wall, where this electrode is positioned to be outside of, but adjacent to, the left ventricle 134. By way of example, an electrode located in the coronary vein may be positioned at location 146. When an electrode is positioned in the coronary vein proximate to the left ventricle at location 146, an ECI vector 148 may be created between electrodes at locations 142 and 146. The ECI vector 148 may be referred to as a pulmonary-centric ECI vector due to the correlation of the vector 148 and the pulmonary veins and arteries 120 and 124.

Alternatively, the electrode within the coronary vein may be shifted further along the coronary vein to a position proximate location 150 and configured to operate with an electrode at location 140 at the SVC to form an ECI vector 152. The vectors 144, 148 and 152 substantially extend through non-cardiac tissue such that impedance variations that are detected along the vectors 144, 152 and 148 correlates closely to changes in the volume of blood flow through the greater vessels 116. As a further option, a combination of the vectors 144, 148 and 152 may be used to measure impedance. As a further option, alternative ECI vectors may be used in place of, or in combination with, the ECI vectors 144, 148 and 152.

Impedance measurements detected along ECI vectors 144, 148 and 152 closely correlates to cardiac output and the mechanical behavior of the heart. In general, tissue has higher resistance than blood. During systole, blood is injected into the thoracic periphery (which includes the greater vessels). Hence, the tissue of the greater vessels between the extra-cardiac electrodes (such as at locations 140, 142, 146 and 150) becomes engorged with blood. Thus, the impedance along the ECI vectors 144, 148 and 152 decreases. During diastole, the amount of blood in the greater vessels decreases. Hence, the impedance along the ECI vectors 144, 148 and 152 increases. Impedance measurements along the ECI vectors 144, 152 and 148 increase and decrease based upon the amount of blood that is injected into the greater vessels 116.

Next, embodiments are described that utilize the ECI impedance to assess hemodynamic performance and provide or suspend therapy based on the assessment.

Extra-Cardiac Impedance Baseline

In accordance with embodiments of the present invention, processes and systems are described by which baseline blood pressure and stroke volume are calculated based on baseline ECI impedance measurements. The baseline hemodynamic status of a patient is determined and compared to subsequent ECI impedance measurements at various times in connection with different types of assessments. For example, the baseline and continuous hemodynamic status of a patient may be assessed in connection with automatic control of an IMD to adjust the operation of the IMD to better improve an individual patient's cardiac output, including adjusting cardiac pacing conditions.

Figure 2:
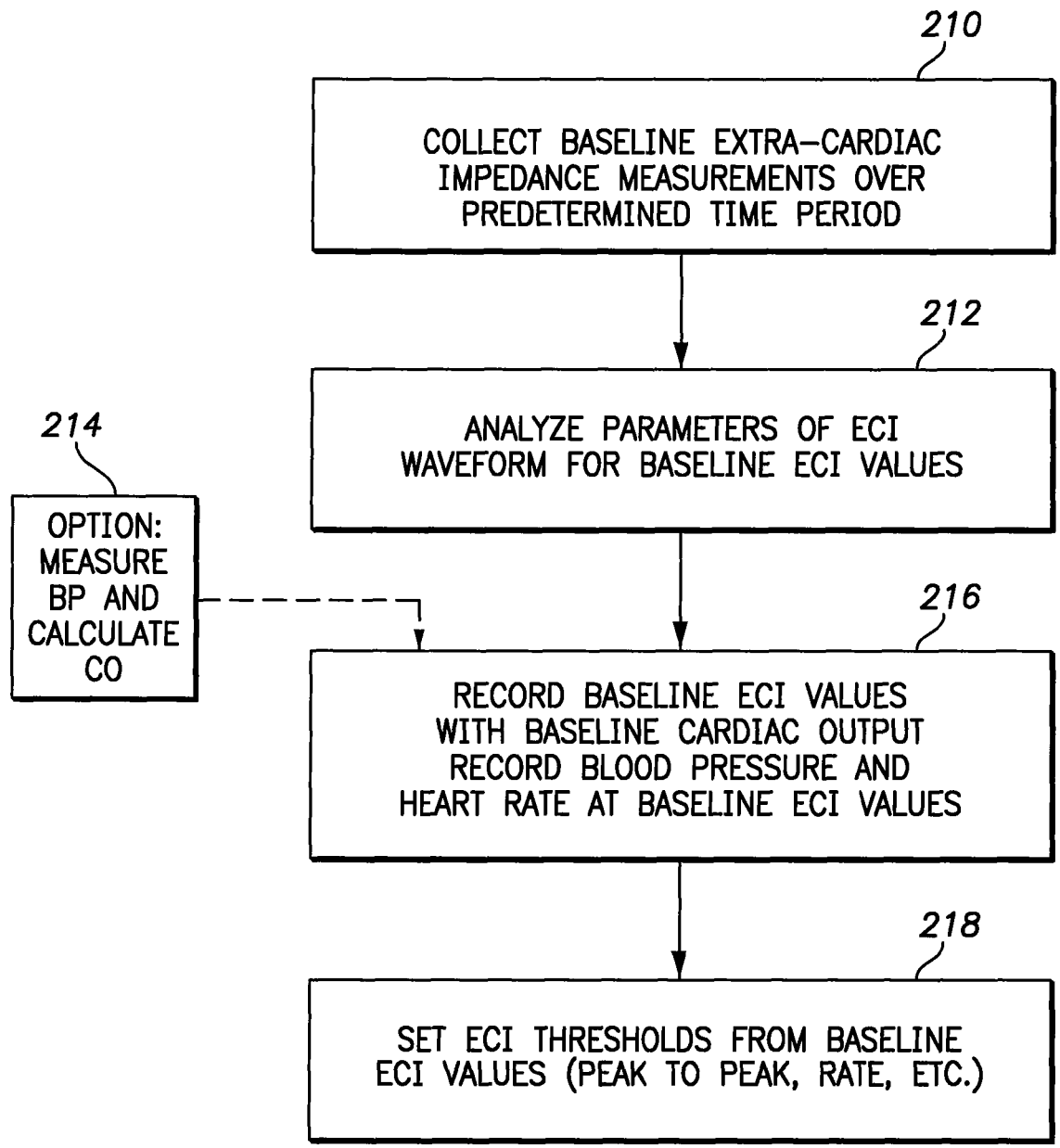
FIG. 2 illustrates a process for collecting baseline extra-cardiac impedance measurements and developing baseline parameters for subsequent use during operation and analysis of cardiac output in accordance with an embodiment.

FIG. 2 illustrates a process for collecting baseline extra-cardiac impedance measurements and developing baseline parameters for subsequent use during operation, analysis of cardiac output and therapy. In FIG. 2, beginning at 210, the process collects baseline ECI measurements over a predetermined period of time from two or more impedance electrodes located outside of the heart. The ECI impedance measurements are taken in connection with an ECI vector that extends through at least a portion of the greater vessels surrounding the heart.

Figure 3:
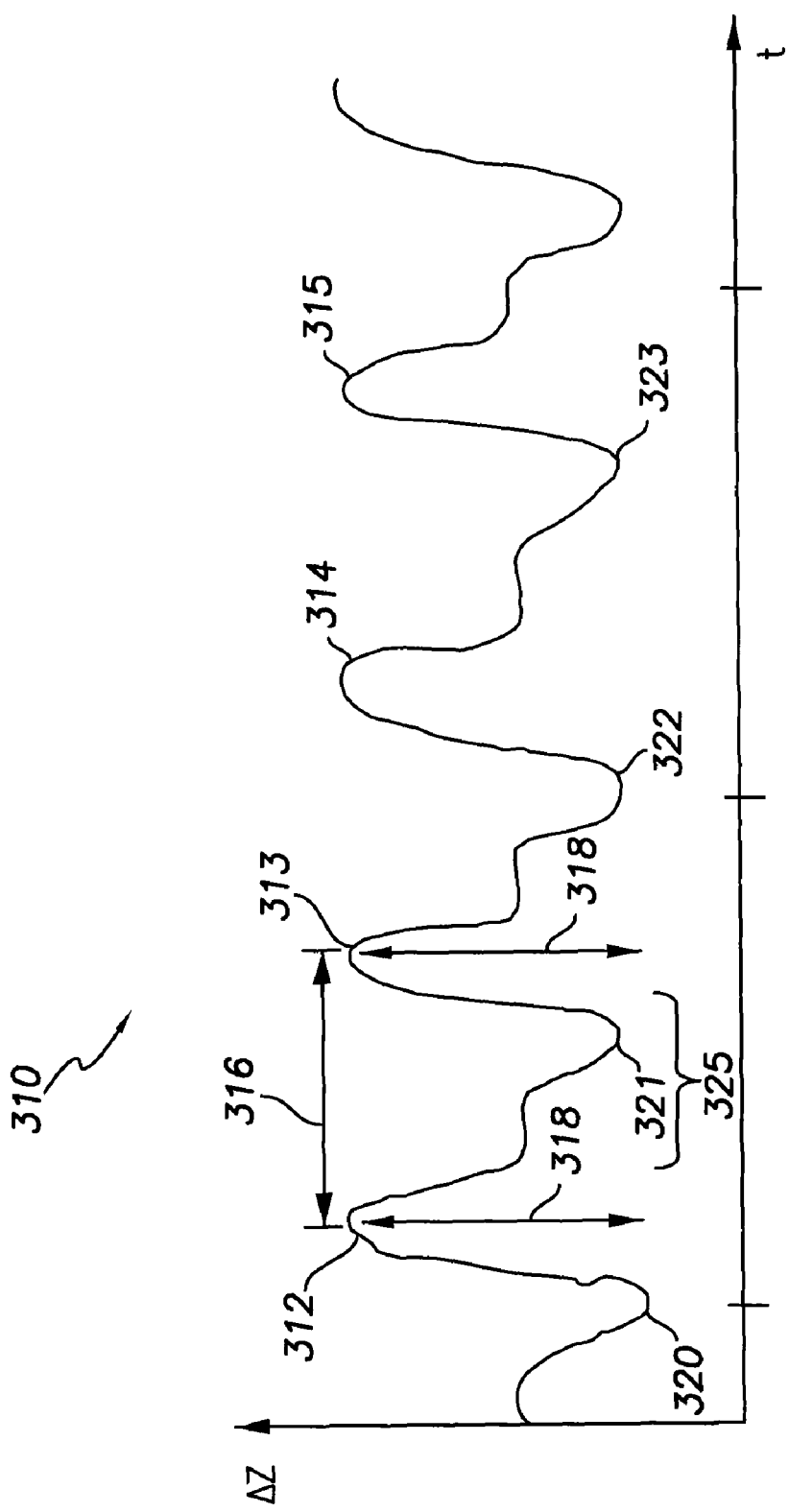
FIG. 3 illustrates a baseline ECI waveform produced from ECI measurements over a predetermined time period in accordance with an embodiment.

FIG. 3 illustrates a baseline ECI waveform 310 produced from ECI measurements over a predetermined time period. The ECI waveform 310 is associated with a normal heart having no arrhythmia and exhibiting a physiologic (healthy) cardiac output pattern or behavior over time. The ECI waveform 310 is shown for a series of four cardiac cycles, but may be longer or shorter. The vertical axis in the graph of FIG. 3 corresponds to an impedance difference $\Delta Z$. Consistent with impedance cardiography, the axis for $\Delta Z$ represents a decrease in impedance when moving upward. Therefore, the abscissa is inverted. The ECI waveform 310 includes peaks 312-315 that are generally evenly spaced from one another by an interval 316. Each of the peaks 312 has peak to peak amplitude 318 between the positive peaks 312-315 and the preceding corresponding minimal peaks (valleys) 320-323. In the example of FIG. 3, the peak to peak amplitudes or distances 318 are substantially similar for each heart cycle. A bracket 325 denotes the interval between the peaks 312 and 313. During normal cardiac behavior, the waveform pattern of $\Delta Z$ within the region 325 may exhibit relatively small changes in amplitude with no or few shifts in the slope or direction of $\Delta Z$. It should be realized that the intervals 316 may not be the same and the peak to peak amplitudes 318 may not be the same, yet the heart may still be healthy and exhibiting a normal cardiac output. The waveform 310 is also modulated by breathing because the intra-thoracic pressure changes. These minor changes may be averaged out over several respiratory cycles or the signals may be sampled with the peaks and valleys identified on the respiratory component of the $\Delta Z$ waveform. Either method is useful for working with the respiratory variations in the cardiac $\Delta Z$ waveform.

Returning to FIG. 2, once the ECI waveform 310 is obtained at 210, flow moves to 212. At 212, the process analyzes a predetermined set of parameters associated with the ECI waveform 310 to determine baseline ECI values. The baseline ECI values are used to define desired characteristics of a baseline ECI waveform or pattern. By way of example, the parameters may correspond to the peak to peak amplitude 318, the interval 316, the number of slope changes within the inter-peak region associated with bracket 325 and the like. The parameters may also include a measure of the regularity of the ECI pattern or waveform. The regularity represents the symmetry within the pattern for successive heart cycles. For example, the symmetry may be based on whether adjacent peaks or a series of peaks are separated by intervals 316 that are within a desired range from one another. The symmetry may be based on whether the intervals 316 are generally equal in length and/or fall within interval threshold limits. The symmetry may be based on whether the peak to peak amplitudes are within a desired range from one another, or are generally equal, and/or fall within peak to peak amplitude threshold limits. A combination of the above factors may be used, as well as other factors, to measure the regularity of an ECI pattern or waveform.

Once the baseline ECI values are obtained at 212, the baseline ECI values are recorded at 216 along with any other baseline information related to cardiac output. For example, an optional operation may be provided at 214 where the blood pressure is directly measured and cardiac output calculated. When the blood pressure is measured at 214, the blood pressure may be recorded at 216 along with the corresponding baseline ECI values. At 216, the heart rate at the baseline ECI values may also be recorded.

Next, at 218, ECI thresholds are set based upon the baseline ECI values. ECI thresholds may represent limits that, when exceeded, are indicative of unduly low or otherwise unacceptable hemodynamic performance. For example, when the peak to peak distance or amplitude is measured during a normal heart cycle, a peak to peak (P-P) threshold may be set as a percentage of the normal or baseline peak to peak amplitude. Thereafter, when a subsequently measured ECI pattern exhibits P-P amplitude that falls below the baseline P-P amplitude by more than the ECI threshold, the cardiac output may be deemed too low or insufficient. As a further option, a regularity threshold may be established in which peaks in the ECI waveform must occur within some percentage of the baseline regularity. Otherwise, the system may determine that insufficient cardiac output is being delivered and therapy is warranted. The ECI thresholds and baseline ECI values are used in various applications and systems as described hereafter.

Embodiments are described herein, whereby impedance is measured along various ECI vectors to detect changes in the impedance of the greater vessels around the heart. Optionally, the changes in impedance may be recorded as one or more impedance profiles reflecting changes in impedance along one or more ECI vectors over the cardiac cycle. The impedance profile(s) may be used to assess hemodynamic performance (HDP), such as cardiac output, over one or more cardiac cycles. The cardiac output represents an amount (e.g. in ml) of blood output by the heart per unit of time (e.g. per minute). For example, if an individual's stroke volume is 80 ml/stroke and the heart rate was 60 beats per minute, then the cardiac output would be 4800 ml/minute. The cardiac output is a function of the change in impedance $\Delta Z$ along an ECI vector. For example, the cardiac output (CO) is proportional to $\Delta Z$ times the mechanical heart rate (also referred to as the pulse rate). Embodiments calculate CO based on the $\Delta Z$ and mechanical HR.

Various embodiments utilize the hemodynamic performance derived from ECI measurements for different purposes. In one embodiment, an ECI derived hemodynamic performance may be used to accelerate delivery of a therapy that would otherwise not yet have been delivered based on intra-cardiac indicators (ICI). In one embodiment, the ECI derived hemodynamic performance may be used to postpone a therapy that would have been delivered based on conventional ICIs. In another embodiment, the ECI derived hemodynamic performance may be used to automatically adjust the operating parameters of an IMD post-implant in an effort to improve the hemodynamics of the patient. For instance, in a biventricular pacing system, AV delay and the V-V delay as well as the base pacing may be adjusted to optimize cardiac output. In another embodiment, the ECI derived hemodynamic performance may be obtained and utilized intraoperatively, such as during implantation of an IMD, to assist in identifying a preferred IMD/lead configuration and to determine how to better position an IMD and the leads to achieve a desired level of device induced hemodynamics. In another embodiment, a multipolar LV pacing lead having two or more electrodes may be paced on one electrode or combinations of electrodes and the multielectrode configuration that yields optimal or preferred hemodynamics may be selected as the preferred or selected therapeutic LV stimulation mode. In another embodiment, the ECI derived hemodynamic performance may be utilized intra-operatively to determine whether to expand the indications for an individual patient who was initially indicated for a single chamber, defibrillator, to instead receive a CRT device. This may be achieved by intra-operatively evaluating whether biventricular pacing significantly improves hemodynamic function.

ECI Based IMD Therapy Confirmation

Figure 4:
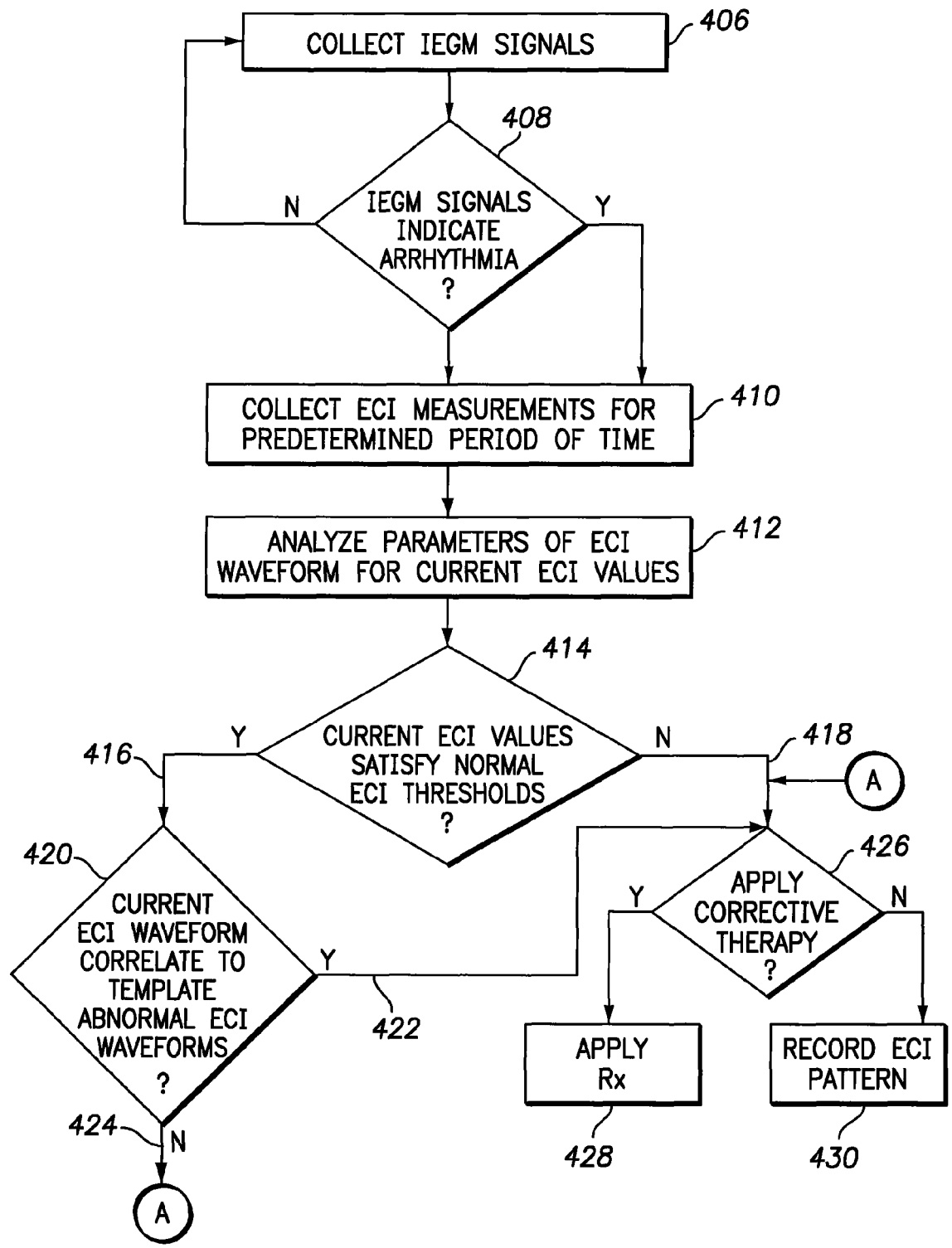
FIG. 4 illustrates a process carried out in accordance with an embodiment to control operation of an IMD based on real-time ECI measurements.

FIG. 4 illustrates a process carried out in accordance with an embodiment to control operation of an IMD based on real-time ECI measurements. In the process of FIG. 4, it is determined whether a corrective therapy is warranted.

Beginning at 406, IEGM signals are collected from IEGM electrodes. The IEGM electrodes may include at least one intra-cardiac electrode that is/are located within the heart. The IEGM electrodes may also include the housing of the IMD which is located outside of the heart. At 408, the process analyzes the IEGM signals utilizing an arrhythmia detection algorithm. The process declares an arrhythmia episode or a normal rhythm based on the analysis of the IEGM signals. At 408, when an arrhythmia episode is declared, the process also determines what therapy is appropriate. The therapy is an IEGM based therapy. Next, at 410 the process collects ECI measurements.

Optionally, the IEGM signal collection and analysis at 406 and 408 may be replaced with another type of intra-cardiac indicator (ICI), such as heart sounds or blood pressure. Optionally, the operations at 406 and 408 may be removed entirely, and instead, the process of FIG. 4 may begin at 410.

At 410, current ECI measurements are collected for a predetermined period of time. ECI measurement collection may be performed continuously throughout operation of the IMD. Alternatively, ECI measurement collection may be conducted only when another arrhythmia detection algorithm identifies a potential arrhythmia. As a further option, the ECI measurements may be performed periodically, when the patient's heart rate exceeds a predetermined threshold or under the instruction of an external programmer and the like.

Figure 5:
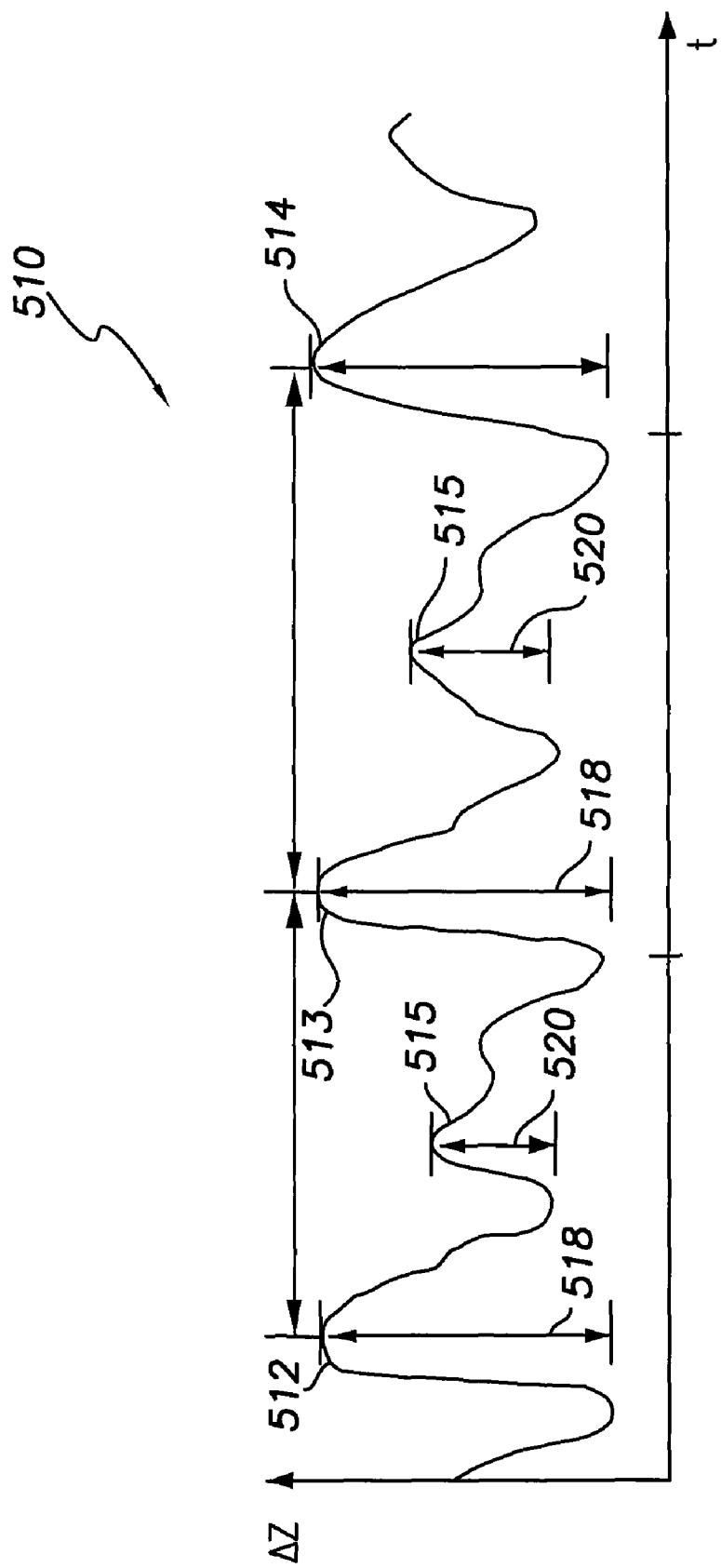
FIG. 5 illustrates an example of an ECI waveform or pattern that may be collected as a current ECI measurement in accordance with an embodiment.

FIG. 5 illustrates an example of an ECI waveform or pattern 510 that may be collected as a current ECI measurement. The ECI waveform 510 of FIG. 5 is indicative of pathologic or abnormal cardiac output. In FIG. 5, the ECI waveform 510 exhibits a pattern referred to as an "alternan". The "alternan" within the cardiac output is characterized by the repetitive pattern of a series of large peaks 512-514 that are separated by smaller local peaks 515 and 516. When the ECI waveform 510 is analyzed, peak to peak amplitude 518 is measured for certain peaks (e.g. 512 and 513). A smaller peak to peak amplitude 520 is measured in connection with the local peaks 515 and 516 which occur between the larger peaks 512-514. When this repetitive pattern of larger and smaller peaks is identified, it is classified as an alternan which is indicative of abnormal cardiac output.

Returning to FIG. 4, once the ECI measurements are collected, flow moves to 412 where desired parameters are analyzed in connection with the ECI waveform to obtain current ECI values. At 414, the current ECI values are compared to the ECI thresholds (such as derived in connection with the process of FIG. 2). When the current ECI values fall within or satisfy the normal ECI thresholds, the comparison at 414 determines that the current ECI waveform is indicative of acceptable or normal cardiac output and thus flow moves along 416. Alternatively, when the ECI values do not satisfy the normal ECI thresholds, it is determined at 414 that the current ECI waveform is indicative of an unhealthy and abnormal cardiac output. Thus, flow moves along 418.

When flow moves along 416, a secondary test may be performed at 420. At 420, the current ECI waveform is compared (such as through correlation or cross correlation) to one or more templates that may be associated with known abnormal ECI waveforms. The templates may be derived from modeling, from past studies of other patients, from past actual cardiac output measurements of the current patient and the like. When the current ECI waveform is found to correlate well to one of the templates for abnormal ECI waveforms, flow moves along 422 to 426. Otherwise, flow moves along 424. The analysis at 420 represents a secondary hemodynamic performance validation which seeks to further analyze the cardiac output for known behavioral abnormalities. Optionally, the test at 420 may be omitted entirely. Instead, when flow moves along 416 the process may return to its initial setting and no further action may be taken.

Returning to 414, when the current ECI values do not satisfy the ECI thresholds, flow moves along 418 to 426. When flow moves along path D18, it is generally because the amount of hemodynamic performance is considered to be too low and unhealthy if left unchecked. At 426, it is determined whether to apply some type of corrective therapy. When a corrective therapy is to be applied, the therapy is applied at 428. The corrective therapy at 428 may be based on IEGM signals, or the ECI measurements or a combination thereof. Otherwise, at 426, it is determined that no therapy should be applied and instead the ECI waveforms are recorded along with other physiologic information at 430. Thus, in the embodiment of FIG. 4, the ECI information is used to confirm or deny a determination based on IEGM signals that a therapy is warranted.

Figure 6:
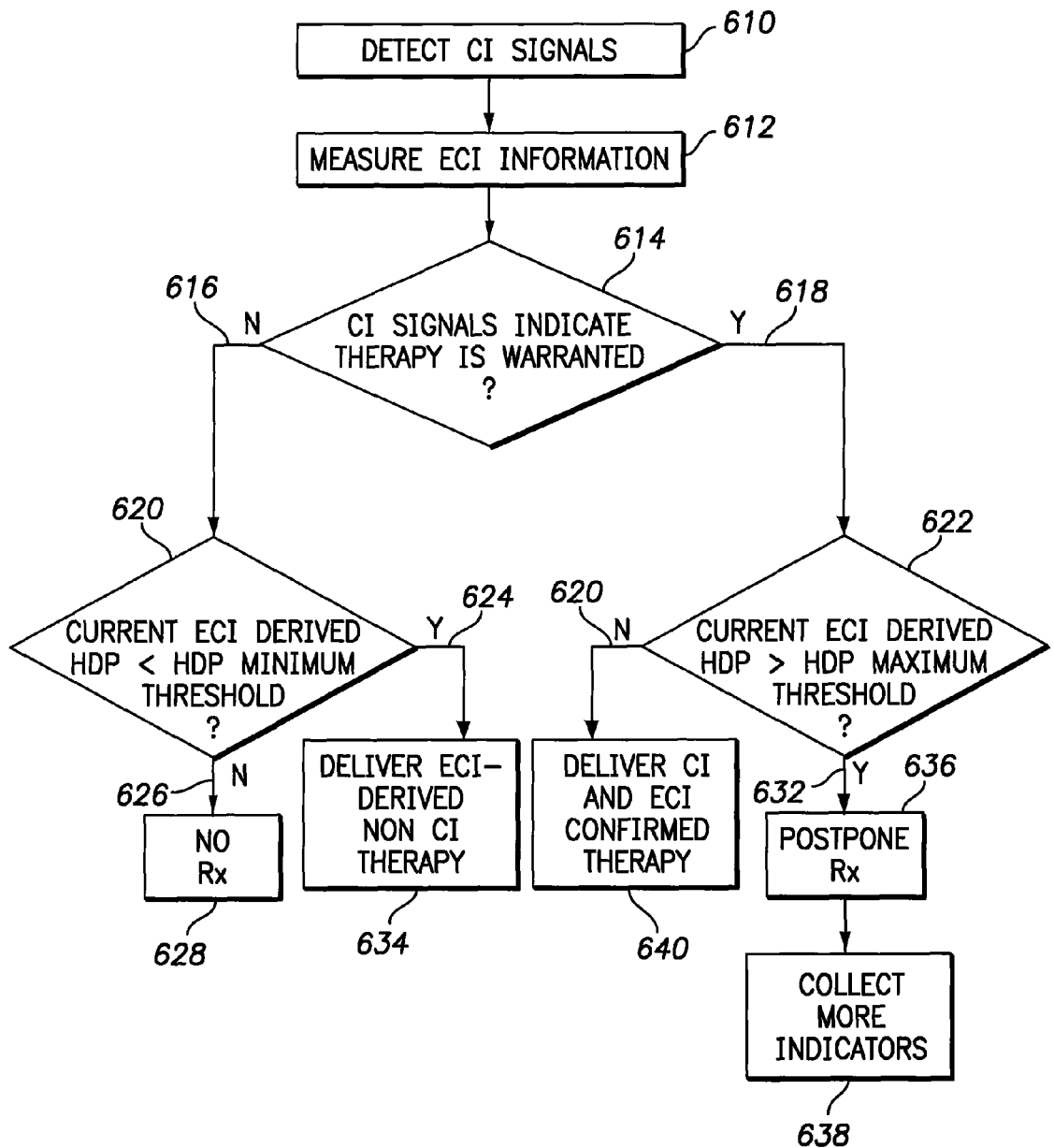
FIG. 6 illustrates a flow chart for an ECI based therapy confirmation process in accordance with an embodiment.

FIG. 6 illustrates a flow chart for an ECI based therapy confirmation process according to an alternative embodiment. The therapy confirmation process of FIG. 6 seeks to confirm, based on ECI measurements, a prior determination as to whether to deliver therapy, where the prior determination was based on another, non-ECI cardiac indicator (CI). The cardiac indicator may be an intra-cardiac indicator (ICI), such as IEGM signals, heart sounds, blood pressure and the like. The cardiac indicator may be an extra-cardiac indicator. The process of FIG. 6 also seeks to determine what type of therapy should be delivered, where the therapy-type determination may be based on ECI-derived information, non-ECI-derived cardiac information (e.g., IEGM derived information, blood pressure information, heart sound information, etc.), or a combination thereof.

At 610, one or more non-ECI cardiac indicators (CI) are detected, such as IEGM signals, blood pressure, heart sounds, ECI signals and the like, through sensing electrodes that are located within the heart. For example, IEGM signals may be detected along sensing vectors that traverse substantially through the heart (e.g. RV to RA, RV to CAN, RA to CAN, RV to LV, etc.). At 612, ECI measurements are detected along an ECI vector. At 614, the cardiac indicators are analyzed (e.g. ICI signals are analyzed using a conventional arrhythmia detection algorithm) to determine whether aCI-derived therapy is warranted. For example, in a pacemaker, atrial or ventricular electrical activity may be sensed to determine when atrial and/or ventricular pacing pulses should be delivered. As another example, in a CRT device, atrial and/or ventricular electrical activity is sensed to identify, among other things, an overly fast rate in the left atrium, left ventricle, etc., lack of synchrony between atrial and ventricular activity, and the like. In a shock only defibrillator, atrial and/or ventricular electrical activity is sensed to identify fibrillation or tachycardia.

At 614, the arrhythmia detection algorithm analyzes the CI information. The arrhythmia detection algorithm renders a non-therapy judgment when the CI information indicates that a normal rhythmic episode occurred. When a normal rhythmic episode is identified, flow passes along path 616 which represents an ECI-based corroboration routine through which ECI information is used to determine directly the actual amount of hemodynamic performance. Path 616 analyzes the ECI information to determine whether insufficient hemodynamic performance exists and thereby warrants over-ruling of the non-therapy judgment. When the ECI information indicates that insufficient hemodynamic performance exists, an ECI-based therapy is declared. The path 616 may confirm aCI based non-therapy judgment, or the path 616 may initiate an ECI based therapy. At 620, the ECI measurement is analyzed to derive a hemodynamic performance (HDP). The ECI derived HDP is compared to a HDP minimum threshold. When the hemodynamic performance is above the HDP minimum threshold, then the patient's hemodynamic performance is deemed to be sufficient and does not warrant therapy. When sufficient HDP is determined at 620, flow moves along 626 to 628 where the final determination is that no therapy is warranted. Optionally, at 628, the ECI measurements may be recorded and/or used to update baseline ECI measurements that correspond to normal rhythmic behavior.

At 620, when the ECI derived HDP is below the minimum predetermined threshold, then the patient's hemodynamic performance is deemed too low or insufficient which does warrant therapy. Hence, flow moves from 620 along 624 to 634 where a therapy is delivered. The therapy delivered at 634 is an ECI-based therapy that is un-confirmed through ICI information (or non-ICI).

Returning to 614, when the arrhythmia detection algorithm declares that the CI information identifies an arrhythmia episode, then a CI-based therapy is indicated, and flow passes along path 618. Path 618 represents an ECI-based confirmation routine through which ECI information is used to determine the amount of hemodynamic performance. Path 618 analyzes the ECI information to determine whether sufficient cardiac output exists to over-rule or suspend the CI-based therapy. The hemodynamic performance is analyzed to confirm, postpone, delay or otherwise decelerate a CI-derived therapy. At 622, the ECI-derived HDP is analyzed to determine whether a patient's hemodynamic performance is sufficient, even through a CI derived therapy has been declared. When the ECI-derived HDP exceeds the HDP threshold, flow moves along path 632 to 636. At 636 the CI-derived therapy is postponed and at 638 the process collects additional information such as more CI information and the like. When at 622, the ECI-derived HDP is determined to fall below the HDP maximum threshold, the flow moves along 630 to 640 where the CI-derived, ECI-confirmed therapy is delivered.

The HDP maximum threshold utilized at 622 and the HDP minimum threshold utilized at 620 may be the same or different values. For example, the HDP maximum threshold may be set to a higher value that the HDP minimum threshold. The HDP maximum threshold, utilized at 622, is being considered in the context of a cardiac episode that has already been declared to be arrhythmic based on CI information. Therefore, the HDP maximum threshold may be set at a level sufficiently high to ensure sufficient hemodynamic performance before suspending, delaying or over-ruling a CI based therapy. Similarly, the HDP minimum threshold, utilized at 620, is being considered in the context of a cardiac episode that has already been declared to be a normal rhythmic episode based on CI information. Therefore, the HDP minimum threshold may be set at a level sufficiently low to ensure insufficient hemodynamic performance before declaring an ECI based therapy when the CI information indicates that no CI based therapy is warranted.

The ECI-based therapy at 634 and the CI-based, ECI-confirmed therapy at 640 may be the same therapy. Optionally, the ECI-based therapy at 634 may differ from the CI-based, ECI-confirmed therapy at 640. The therapy at 634 is reached because of a determination that the hemodynamic performance is too low, even though CI information indicates that no therapy is warranted. Thus, when a heart exhibits acceptable (physiologic) electrical activity (e.g. detected through IEGM signals), but this electrical activity results in insufficient hemodynamic performance, one type of therapy may be warranted. For example, the therapy may be developed primarily to improve HDP, without changing the existing intrinsic synchrony between the chambers of the heart.

The therapy at 640 is reached because of a determination that the CI information indicates that a therapy is warranted, and the ECI information confirms that the hemodynamic performance is insufficient. Thus, when the heart exhibits un-acceptable (non-physiologic) electrical activity (e.g. detected through IEGM signals), and this electrical activity results in insufficient hemodynamic performance, another type of therapy may be warranted. For example, the therapy may be developed both to improve HDP and change the existing intrinsic non-synchrony between or arrhythmia within the chambers of the heart. Hence, for example, the ECI-based therapy, that is un-confirmed by CI information, may correspond to one type of anti-tachy pacing pattern that may differ from another type of anti-tachy pacing pattern that would be delivered when an IEGM signal indicates an arrhythmia that is confirmed by ECI measurements.

Extra-Cardiac Impedance Monitor

Figure 7:
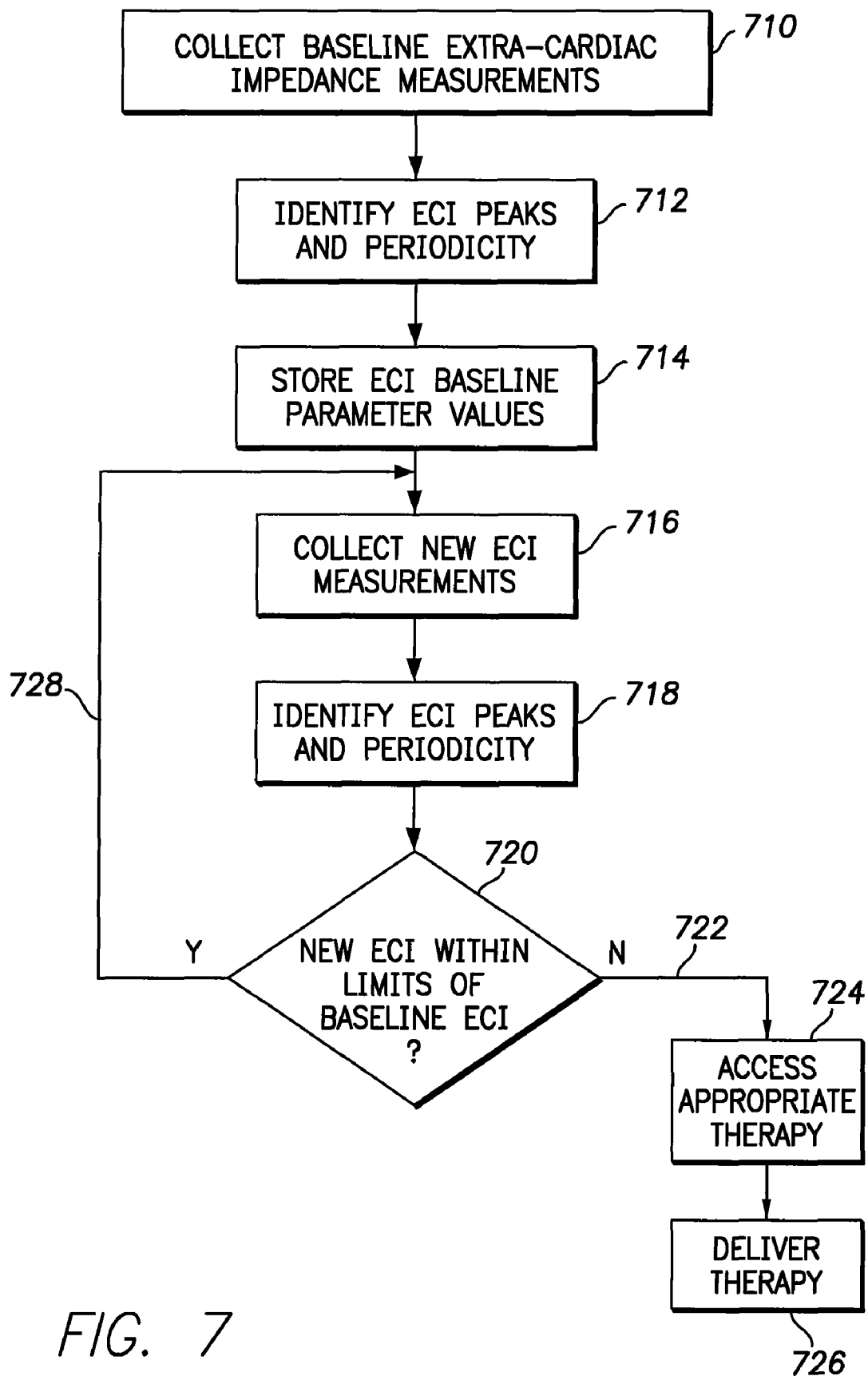
FIG. 7 illustrates a process that may be carried out in connection with an alternative embodiment as a stand-alone ECI monitor.

FIG. 7 illustrates a process that may be carried out in connection with an alternative embodiment as an ECI monitor. The ECI monitor may be in an IMD or an external device. The ECI monitor declares abnormal or pathologic behavior solely based on ECI measurements, without use of intra-cardiac signals, EKG, IEGM signals or other ICI signals. The method of FIG. 7 collects ECI measurements, as a baseline and throughout operation, to determine the baseline and present hemodynamic status of a patient.

Beginning at 710, the method of FIG. 7 collects background extra-cardiac impedance measurements along one or more ECI vectors. At 712 the impedance measurements are plotted over time and certain graphical characteristics are identified therefrom, such as peaks within an ECI waveform and a periodicity of the ECI waveform. Once the ECI waveforms for background impedance measurements are analyzed, the system has a baseline quantity of information to which later measurements may be compared. At 714, the ECI baseline parameter values (e.g., peak amplitudes, dynamic range, periodicity, etc.) are stored.

Next, at 716, the implantable or external device begins to collect new ECI measurements. The ECI measurement collection at R16 may be done periodically or on demand. At 718, the parameter values from the new or current ECI measurements are identified (e.g., the peaks, dynamic range, periodicity, etc.). At 720, the new ECI parameter values are compared with the baseline ECI parameter values. The new and baseline ECI values may differ by some predetermined threshold without being considered pathologic (non-physiologic). When the new ECI values diverge from the baseline ECI values by more than the threshold limits, flow moves along path 722 to 724 at which the process assesses what therapy may be appropriate to be delivered. At 726, the therapy identified at 724 is then delivered.

Returning to 720, when the new ECI values fall within the limits about the baseline ECI values, flow moves along 728 to return to 716. Next, new ECI measurements are collected.

Intra-Operative Hemodynamic Assessment

Figure 8:
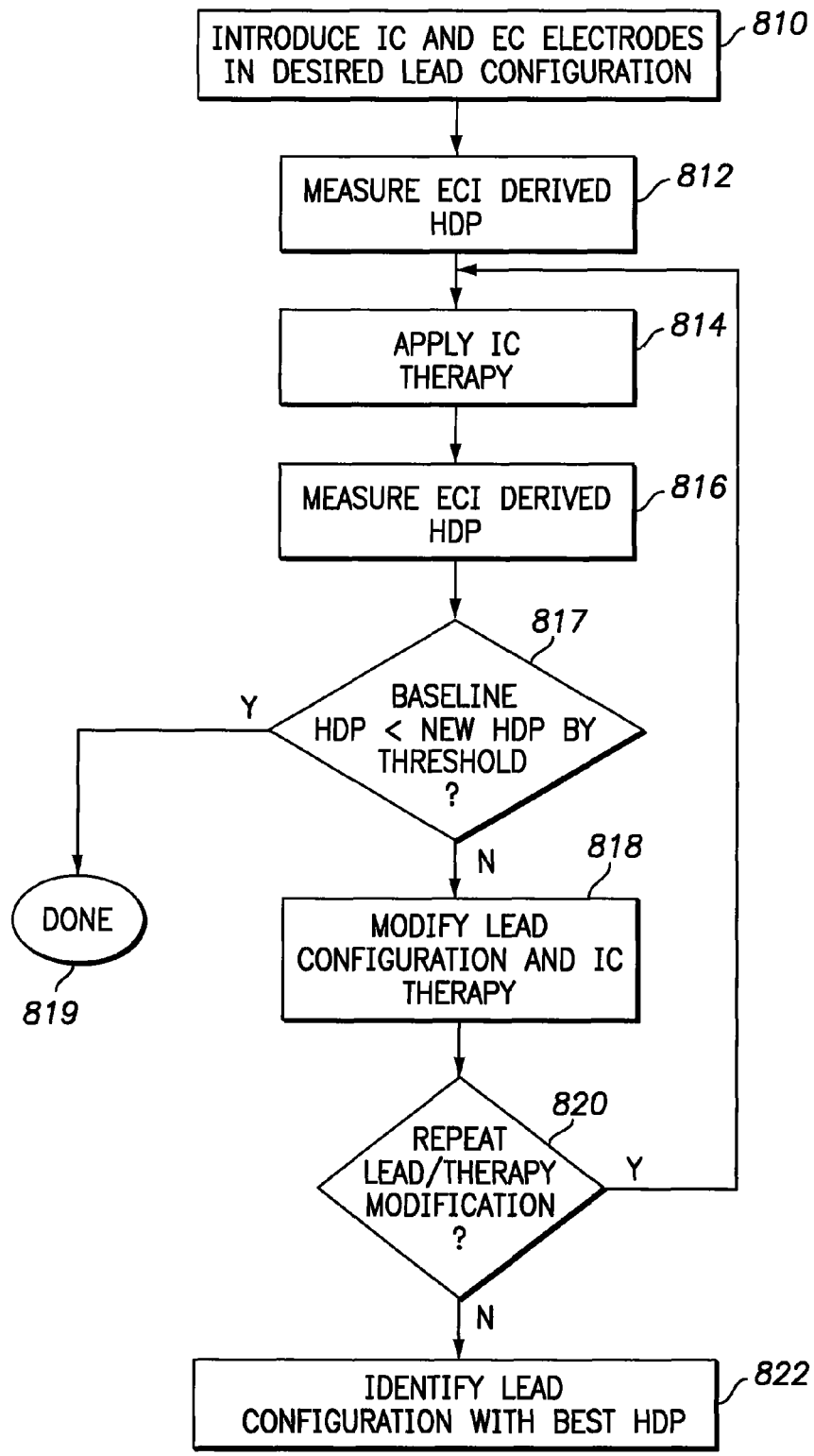
FIG. 8 illustrates a procedure that may be carried out intra-operatively while installing an implantable medical device in a patient in accordance with an embodiment.

FIG. 8 illustrates a procedure that may be carried out intra-operatively while installing an implantable medical device in a patient. Beginning at 810, a physician introduces one or more leads (that collectively are referred to as a lead assembly) into a patient. The leads are introduced based upon a surgical pre-planning determination as to what the preferred lead configuration and placement are for the current patient. These determinations are based upon the patient's indications. The lead assembly includes intra-cardiac (IC) electrodes and extra-cardiac (EC) electrodes. The IC and EC electrodes may be on the same or different leads. For example, one lead may include pacing and/or sensing IC electrodes configured to be located in the right ventricle and/or right atrium. The same lead may include an EC electrode configured to be located in the SVC (e.g., location 140 in FIG. 1). The EC electrode located in the SVC may be utilized to sense extra-cardiac impedance only, or to sense extra-cardiac impedance and intra-cardiac electrical signals. The EC electrodes may be permanent or temporary (to be only used during the intraoperative procedure and then removed). For example, one or more temporary electrodes may be positioned in the locations 140, 142, 146 and/or 150 (FIG. 1). Alternatively the location 140 may be achieved by using an introducer sheath with a distal electrode. Introducer sheaths facilitate lead placement and are typically employed to get access to the vein and to provide a conduit for placing a lead. After lead implantation the introducers are split axially and removed.

Optionally, a temporary electrode may be inserted into a subcutaneous, subclavical area where the IMD will be later placed. The temporary electrode may be used to sense extra-cardiac impedance only, or to sense extra-cardiac impedance and intra-cardiac electrical signals. As a further option, a temporary or permanent electrode may be located in a coronary vein proximate to the left ventricle (e.g. locations 146 or 150 in FIG. 1). The coronary vein electrode may be used to sense extra-cardiac impedance only, or to sense extra-cardiac impedance and intra-cardiac electrical signals. Once the lead (s) are implanted to desired locations, the leads are connected to an external PSA. The PSA has the capabilities to measure intra-cardiac indicators (e.g. IEGM signals, blood pressure, heart sounds, etc.) and to deliver stimulating pulses (e.g. pacing pulses, ATP therapies, defibrillation shocks, etc.). The PSA also has the capability to measure extra-cardiac impedance as discussed herein along various ECI vectors.

At 812, the process measures impedance between at least two extra-cardiac electrodes to obtain baseline ECI measurements. The baseline ECI measurements are used to derive an initial ECI hemodynamic performance while the PSA is not applying any stimulating pulses or therapy. In this example, the baseline ECI measurements correspond to non-IMD-assisted behavior of the heart which may include an arrhythmia or a normal rhythmic pattern.

At 814, the external PSA applies a predetermined therapy to an initial combination/configuration of electrodes on the lead(s). The therapy applied at 814 is set to induce a desired result. At 816, while the therapy is being delivered or immediately after delivery of the therapy, a new current ECI measurement is obtained. The current hemodynamic performance is derived from the current ECI measurements.

Figure 14:
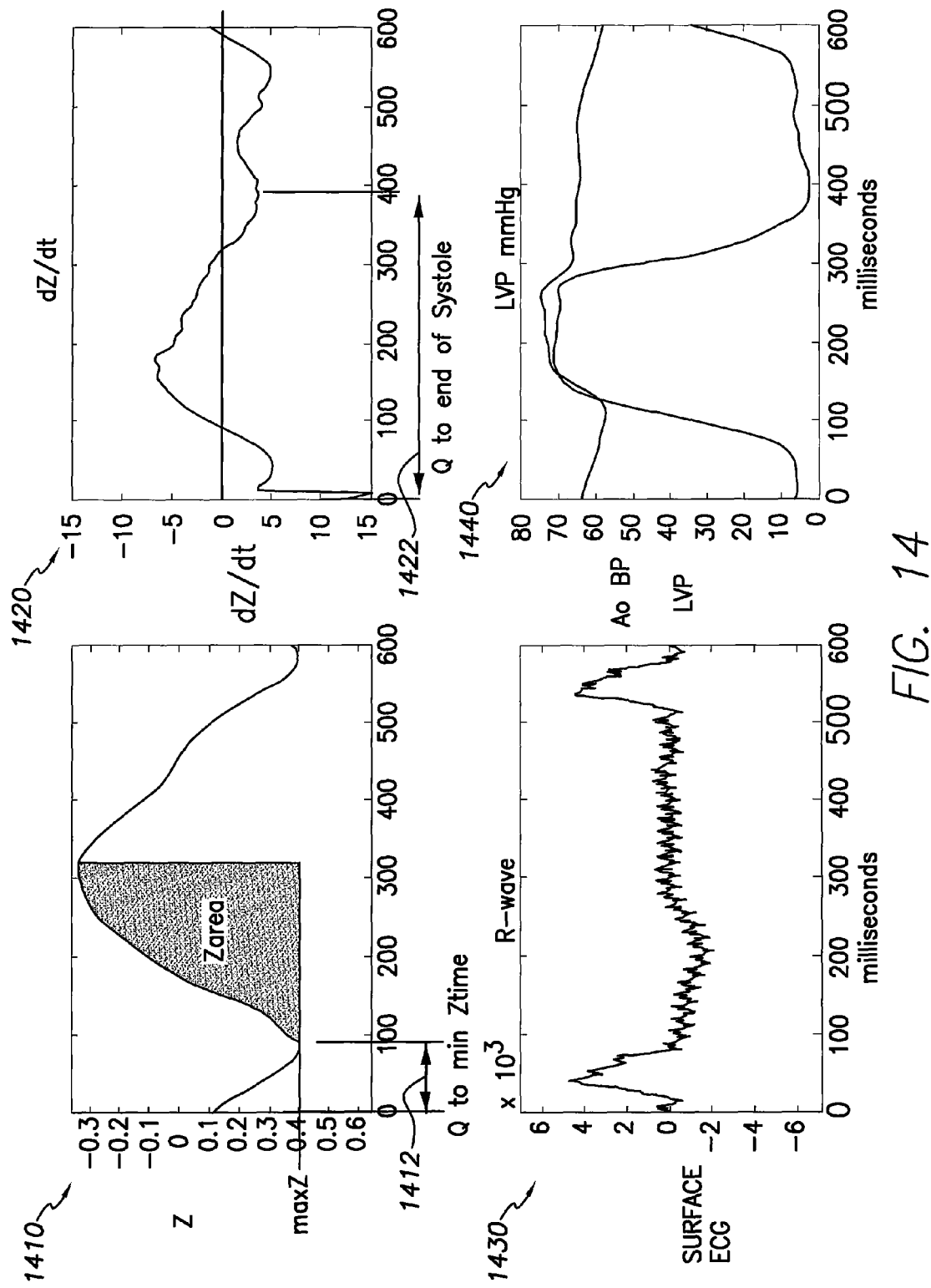
FIG. 14 represents a series of graphs illustrating representative relations between certain impedance features and cardiac signals.
Figure 15:
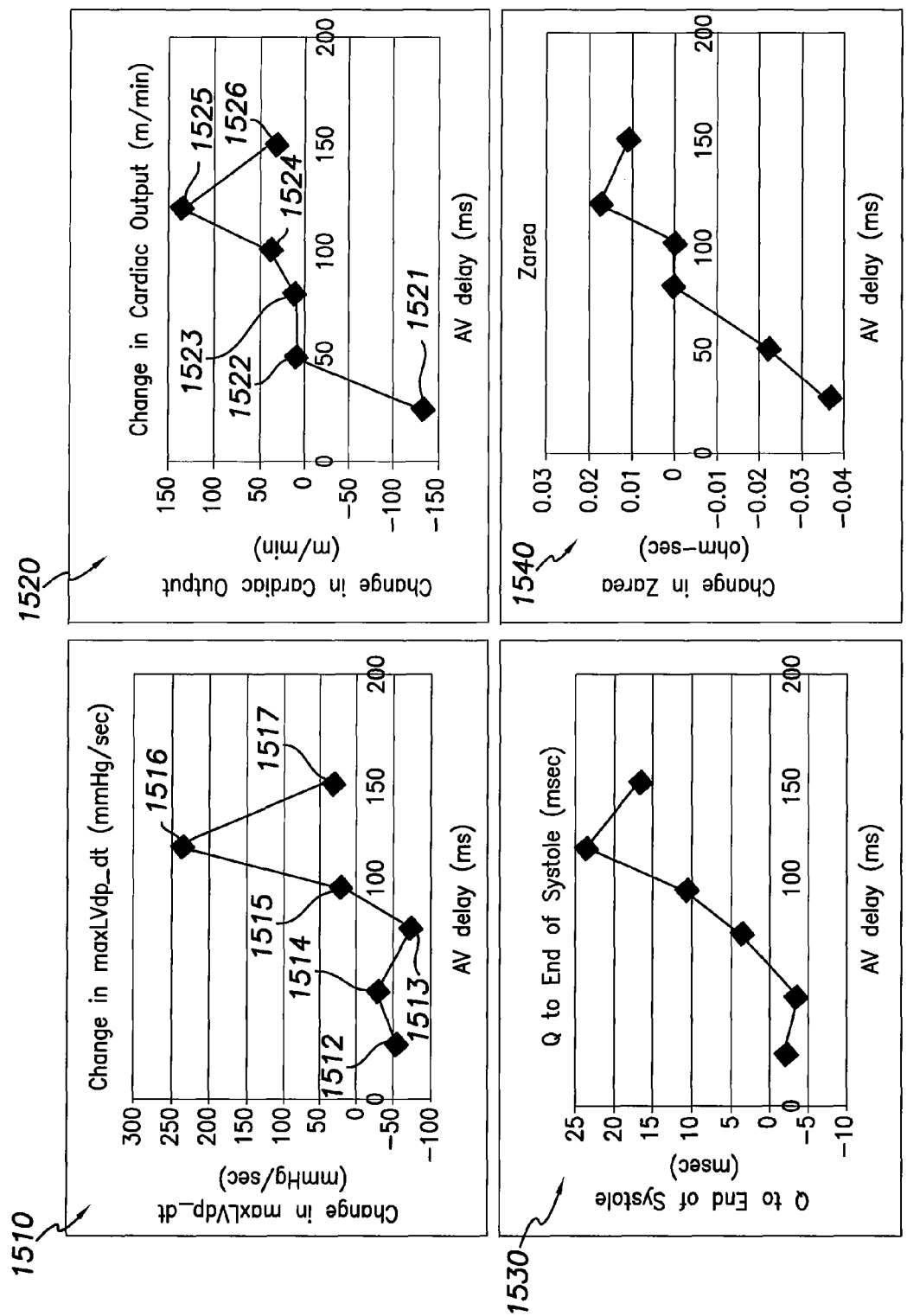
FIG. 15 illustrates data plots that may be displayed on an external device (e.g., a PSA or an external programmer) and used in connection with setting the programmable parameters of an IMD such as programming an AV delay for the IMD.
Figure 16:
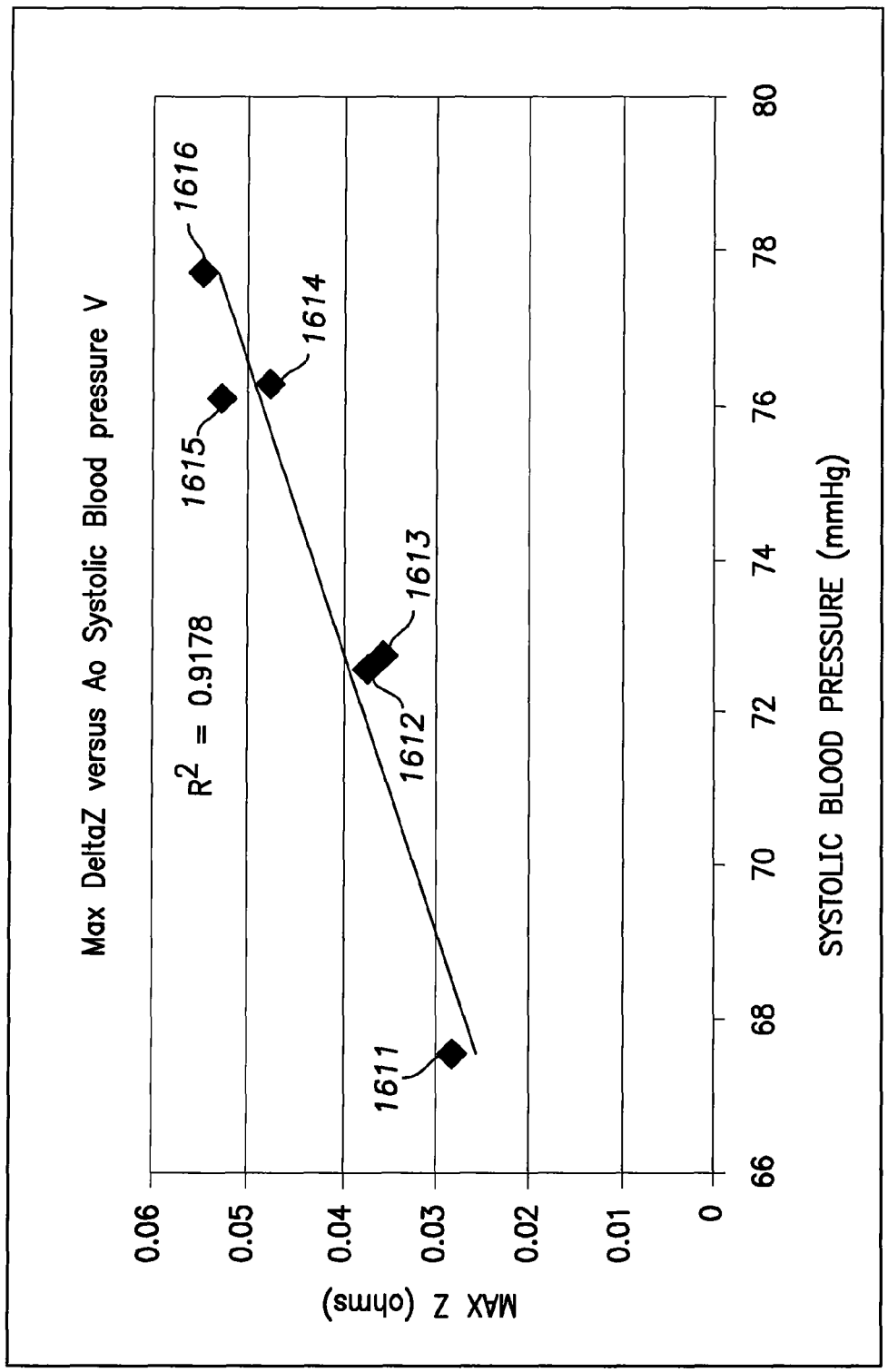
FIG. 16 illustrates an exemplary plot of the maximum change in impedance max$\Delta Z$ relative to the systolic blood pressure.

At 817, the current hemodynamic performance at 816 is compared with the baseline hemodynamic performance obtained at 812. By way of example, the comparison may involve plots or graphs showing impedance parameters over time, such as the change in impedance per unit time ($\Delta Z/\Delta T$) following systole, the maximum impedance maxZ over time following systole, and the like. The graphs may also plot over time, change in maximum LV pressure per unit time (LV $\Delta P/\Delta T$), change in hemodynamic performance, time to end of ejection, change in impedance area (Z area). Each plot may correspond to a different combination of IC lead placement, lead configuration and therapy. The external device may display graphs such as shown in FIGS. 14, 15 and 16 to the physician. The information in the graphs may be manually reviewed by the physician or automatically analyzed to obtain a selected combination of IC lead placement, configuration and therapy.

The relation between the baseline and current hemodynamic performance provides an indication as to whether the present lead position and configuration at 810 and therapy delivered at 814 had a positive impact (e.g., increase) on the hemodynamic performance of a patient. If the hemodynamic performance at 816 improves sufficiently over the hemodynamic performance at 812, no further lead adjustments or IC therapy changes may be warranted, and thus flow moves to 819. However, if the hemodynamic performance measured at 816 does not improve over the baseline hemodynamic performance measured at 812, then flow moves to 818. At 818, the physician modifies the IC lead configuration, IC lead position and/or the IC therapy. For example, the physician may adjust the position of one or more IC leads within a chamber of the heart. Alternatively or in addition, the physician may change the polarity of an IC therapy. At 820, the physician determines whether to apply an additional IC therapy and/or make further lead modifications.

The operations at 814, 816, and 818 are repeated a desired number of times. Optionally, the operations at 814, 816, and 818 may be repeated only until a desired level of HDP is achieved or a desired percentage improvement in HDP is achieved. Once the changes in the lead configuration and/or the IC therapy are made a number of times and the hemodynamic performance is determined a corresponding number of times, flow passes to 822 where it is then determined which lead position, lead configuration and therapy achieve the selected level of hemodynamic performance. Optionally, the operations of 814, 816 and 818 may be stopped as soon as the lead placement, lead configuration and therapy achieve a desired improvement in hemodynamic performance (in terms of percentage or in terms of an absolute HDP amount). At 822, the IMD is then implanted and connected to the lead(s).

As explained above the method of FIG. 8 intra-operatively assesses hemodynamic performance during implantation of an implantable medical device. The method includes providing extra-cardiac (EC) electrodes to be located outside of a heart and positioned to define an extra-cardiac impedance (ECI) vector therebetween where at least a portion of the greater vessels are interposed between the EC electrodes along the ECI vector. The method also includes providing at least one intra-cardiac (IC) lead to be positioned in the heart, and delivering an IC therapy to the heart through the IC lead. Next, the method measures an extra-cardiac impedance between the EC electrodes along the ECI vector to obtain ECI measurements, and determines a hemodynamic performance (HDP) based on the ECI measurements. The physician adjusts at least one of i) an IC lead position, ii) an IC lead configuration and iii) an IC therapy, and the external device repeats the measuring and determining operations. The external device then provides information regarding changes in the HDP relative to each IC lead position, lead configuration and IC therapy in order to identify when at least one of i) the IC lead position, ii) the IC lead configuration and iii) the IC therapy improve cardiac output based on the ECI measurements. This identification may include displaying charts, graphs or raw data regarding impedance and/or cardiac output maximums, changes, etc. for different programmed settings and lead positions.

Optionally, the IC lead may initially represent a single chamber lead for an implantable defibrillator. The adjusting operation may include providing a CRT temporary lead to the patient and then delivering a CRT therapy. The external device then identifies whether the CRT lead and CRT therapy improve the hemodynamic performance of the patient. The external device may measure the ECI measurements before the delivering operation to obtain a baseline ECI measurement and after at least one of the delivering and adjusting operations to obtain subsequent ECI measurements. The external device displays a comparison of hemodynamic performance associated with the baseline and subsequent ECI measurements to identify a final IC lead position and final IC therapy. The external device may calculate successive hemodynamic performance associated with different combinations of the IC lead position and the IC therapy and identify a final IC lead position and a final IC therapy that correspond to a preferred one of the successive hemodynamic performance. The external device may obtain a baseline HDP and a new HDP associated with at least one difference in the IC lead position and the IC therapy, the baseline HDP being compared to the new HDP to determine whether to repeat the measuring, determining and adjusting operations another iteration.

The process of FIG. 8 affords the ability to assess hemodynamic output intra-operatively while implanting an IMD. Lead and therapy configurations may be changed intra-operatively while obtaining a reliable direct indication of the cardiac output achieved by each particular lead position and therapy. The real-time intra-operative hemodynamic assessment improves the responder rate to IMDs.

Expand Indications for CRT Devices

Figure 9:
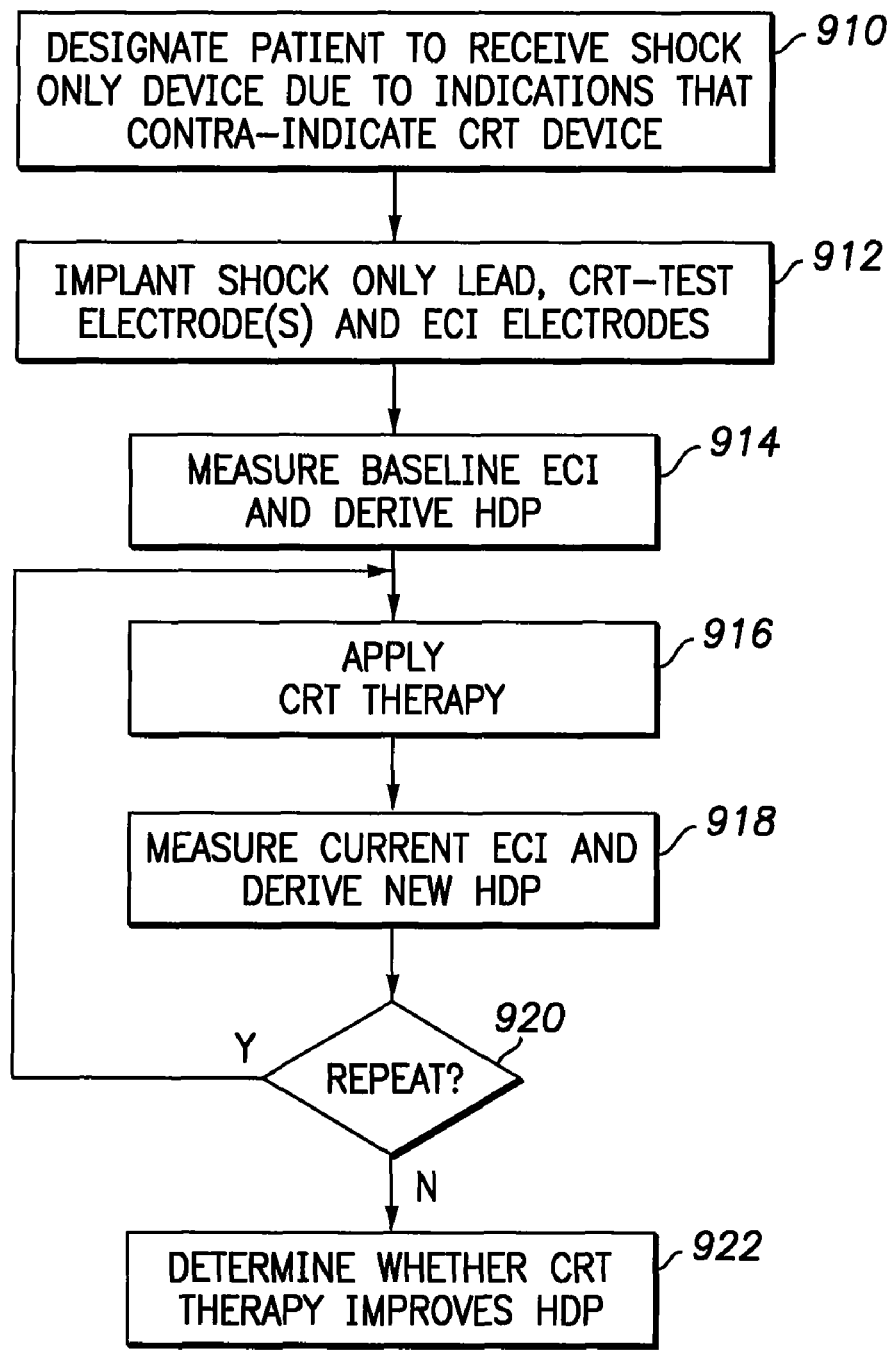
FIG. 9 illustrates a procedure that may be carried out intra-operatively while installing an implantable defibrillator in a patient with indications for a "shock only" device in accordance with an embodiment.

FIG. 9 illustrates a procedure that may be carried out intra-operatively while installing an implantable defibrillator in a patient with indications for a single chamber device. Beginning at 910, the patient is identified to have indications for a single chamber device and to be contra-indicated for a CRT device. For example, the patient may have a narrow QRS complex. At 912, a physician introduces a lead having single chamber electrodes into a patient. The same or a different lead may be introduced to include one or more ECI electrodes outside of the heart. Also, CRT test electrode(s) may be inserted on a temporary lead. The temporary lead may locate the CRT test electrode(s) in various locations within the heart depending upon what type of CRT therapies are desired.

At 914, a PSA is connected and baseline ECI measurements are obtained along one or more ECI vectors. The baseline HDP is derived from the baseline ECI measurements. At 916, a CRT therapy is applied utilizing the CRT test electrodes on the temporary lead and/or the shock electrodes. At 918, a current ECI measurement is obtained and a new HDP is derived from the current ECI measurements. The ECI measurements obtained at 914 represent pre-CRT or non-IMD-assisted ECI measurements in that the baseline ECI measurements correspond to hemodynamic performance that is produced before any CRT therapy is delivered. The ECI measurements obtained at 918 represent post-CRT or IMD-assisted ECI measurements in that the current ECI measurements correspond to hemodynamic performance that is produced after a CRT therapy.

At 920, it is determined whether to repeat the CRT therapy and obtain more ECI measurements. Once a sufficient number of ECI measurements are obtained, flow moves to 922. At 922, the pre-CRT ECI measurements and post-CRT ECI measurements are compared to determine whether the CRT therapy improved the cardiac output. By way of example, the comparison may involve plots or graphs showing impedance parameters over time, such as the change in impedance per unit time ($\Delta Z/\Delta T$) following systole, the maximum impedance maxZ over time following systole, and the like. A first plot may correspond to pre-CRT and a second plot may correspond to post CRT. Each plot may correspond to a different combination of IC lead placement, lead configuration and therapy. The external device may display graphs such as shown in FIGS. 14, 15 and 16 to the physician. The information in the graphs may be manually reviewed by the physician or automatically analyzed to obtain a selected combination of IC lead placement, configuration and therapy.

Based on this comparison, it can then be determined whether there is sufficient indication that the patient would benefit from a CRT device, not just a shock only defibrillation device.

The process of FIG. 9 enables patients to be assessed intra-operatively to determine whether a CRT device would benefit the patient. The intra-operative assessment is based on post-CRT real-time hemodynamic performance measurements and thus is representative of the individual patient's hemodynamic behavior and physiologic response to a CRT device.

Implantable Medical Device

Figure 10:
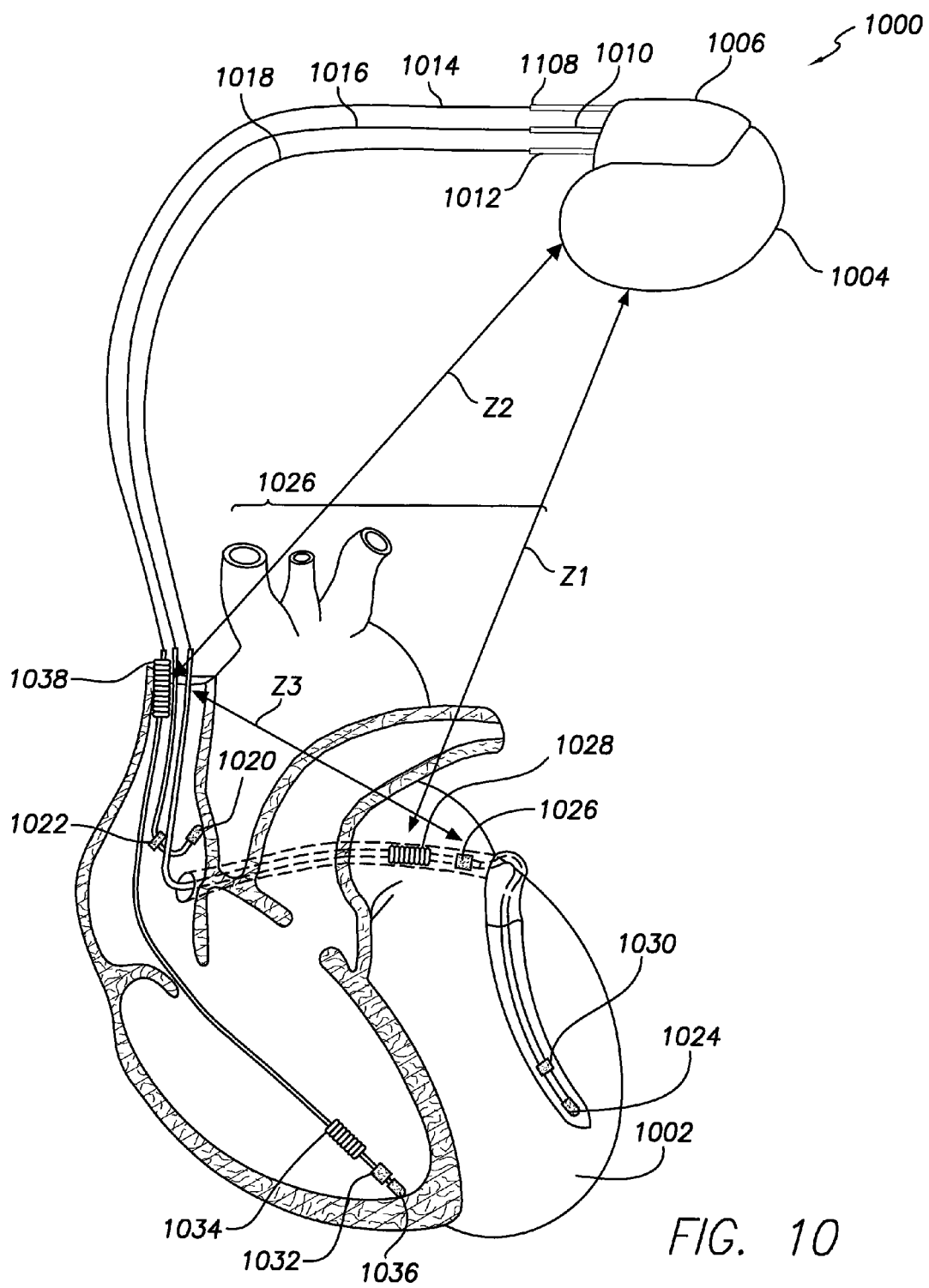
FIG. 10 illustrates an IMD that is coupled to a heart in accordance with an embodiment.

FIG. 10 illustrates an IMD 1000 or external device, such as PSA, that is coupled to a heart 1002. The external device may be connected to leads such as during implantation of an IMD in accordance with the processes described herein to determine a preferred therapy and lead position based on cardiac output. The IMD 1000 may be a cardiac pacemaker, an ICD, a defibrillator, an ICD coupled with a pacemaker, and the like, implemented in accordance with one embodiment of the present invention. The IMD 1000 may be a dual-chamber stimulation device capable of treating both fast and slow arrhythmias with stimulation therapy, including cardioversion, defibrillation, and pacing stimulation, as well as capable of detecting heart failure, evaluating its severity, tracking the progression thereof, and controlling the delivery of therapy and warnings. In accordance with the processes explained herein, the IMD 1000 may be controlled to detect ICI signals and ECI measurements and based thereof, to identify potentially abnormal physiology and insufficient cardiac output.

The IMD 1000 includes a housing 1004 that is joined to a header assembly 1006 (e.g., an IS-4 connector assembly) that holds receptacle connectors 1008, 1010, 1012 that are connected to a right ventricular lead 1014, a right atrial lead 1016, and a coronary sinus lead 1018, respectively. The leads 1014, 1016, and 1018 may be located at various locations, such as an atrium, a ventricle, or both to measure the physiological condition of the heart 1002. One or more of the leads 1014, 1016, and 1018 detect IEGM signals that form an electrical activity indicator of myocardial function over multiple cardiac cycles. To sense atrial cardiac signals and to provide right atrial chamber stimulation therapy, the right atrial lead 1016 has at least an atrial tip electrode 1020, which typically is implanted in the right atrial appendage, and an atrial ring electrode 1022. The IEGM signals represent analog signals that are subsequently digitized and analyzed to identify waveforms or segments of interest. Examples of waveforms or segments of interest identified from the IEGM signals include the P-wave, T-wave, the R-wave, the QRS complex, the ST segment, and the like. The waveforms of interest may be collected over a period of time.

The coronary sinus lead 1018 receives atrial and ventricular cardiac signals and delivers left ventricular pacing therapy using at least a left ventricular ("LV") tip electrode 1024, and delivers left atrial ("LA") pacing therapy using at least a left atrial ring electrode 1026. The coronary sinus lead 1018 also is connected with a LV ring electrode 1030 disposed between the LV tip electrode 1024 and the left atrial ring electrode 1026. The LV ring electrode 1030 may be used as a defibrillation electrode. The right ventricular ("RV") lead 1014 has an RV tip electrode 1036, an RV ring electrode 1032, an RV coil electrode 1034, and an SVC coil electrode 1038. The RV lead 1014 is capable of receiving cardiac signals, and delivering stimulation in the form of pacing, CRT and shock therapy to the right ventricle. The RV coil electrode 1034 may be used as a defibrillation electrode. The housing 1004 may also function as an electrode.

The IMD 1000 measures ECI impedance parameters to monitor and determine variations in the cardiac output in accordance with the processes explained herein. An impedance parameter includes an impedance vector that represents the impedance measured along a path (generally a linear path) between at least two points. One or more impedance vectors measured by the IMD H00 may extend through the greater vessels 1026. The impedance vectors that extend through the greater vessels 1026 represent the impedance of the tissue and the blood along the paths of the impedance vectors. The IMD 1000 may determine the average of an impedance vector for a number of cardiac cycles and compare multiple averages. In a healthy heart 1002, the average impedance vector over time may remain approximately the same over multiple sets of cardiac cycles.

By way of example only, the impedance vectors measured by the IMD 1000 may include one or more of first, second and third ECI impedance vectors Z1, Z2 and Z3 (FIG. 10). The first and second ECI impedance vectors Z1 and Z2 are between the housing 1004 and SVC coil electrode 1038 and the housing 1004 and LA electrode 1028, respectively. The third ECI impedance vector Z3 is between the LA ring electrode 1026 and SVC coil electrode 1038.

The IMD 1000 may calculate one or more of the impedance vectors using a four terminal measurement technique in one embodiment. The four terminal measurement technique may reduce the impact that the intrinsic impedance of the electrodes has on the impedance vector. The intrinsic impedances of the electrodes 1024-1038 may be large when compared to the change ΔZ in the impedance of the greater vessels. For example, the LV and RV electrode tips 1024, 1036 may have intrinsic impedances of 500 ohms or more while the change ΔZ in impedance of the myocardium in the greater vessels may be approximately 50 ohms or less. The four terminal measurement technique can eliminate the intrinsic impedances of the electrodes from the measured impedance vector.

The four terminal measurement technique involves applying a current across a predetermined combination of the electrodes while measuring a voltage between a different combination of the electrodes. As shown in FIG. 10, the current may be supplied between the RV coil electrode 1034 and the LV ring electrode 1030. The voltage is measured between the SVC coil 1038 and housing 1004. The voltage represents the voltage difference measured. Using the voltage and the current, the impedance vector may be calculated.

Figure 11:
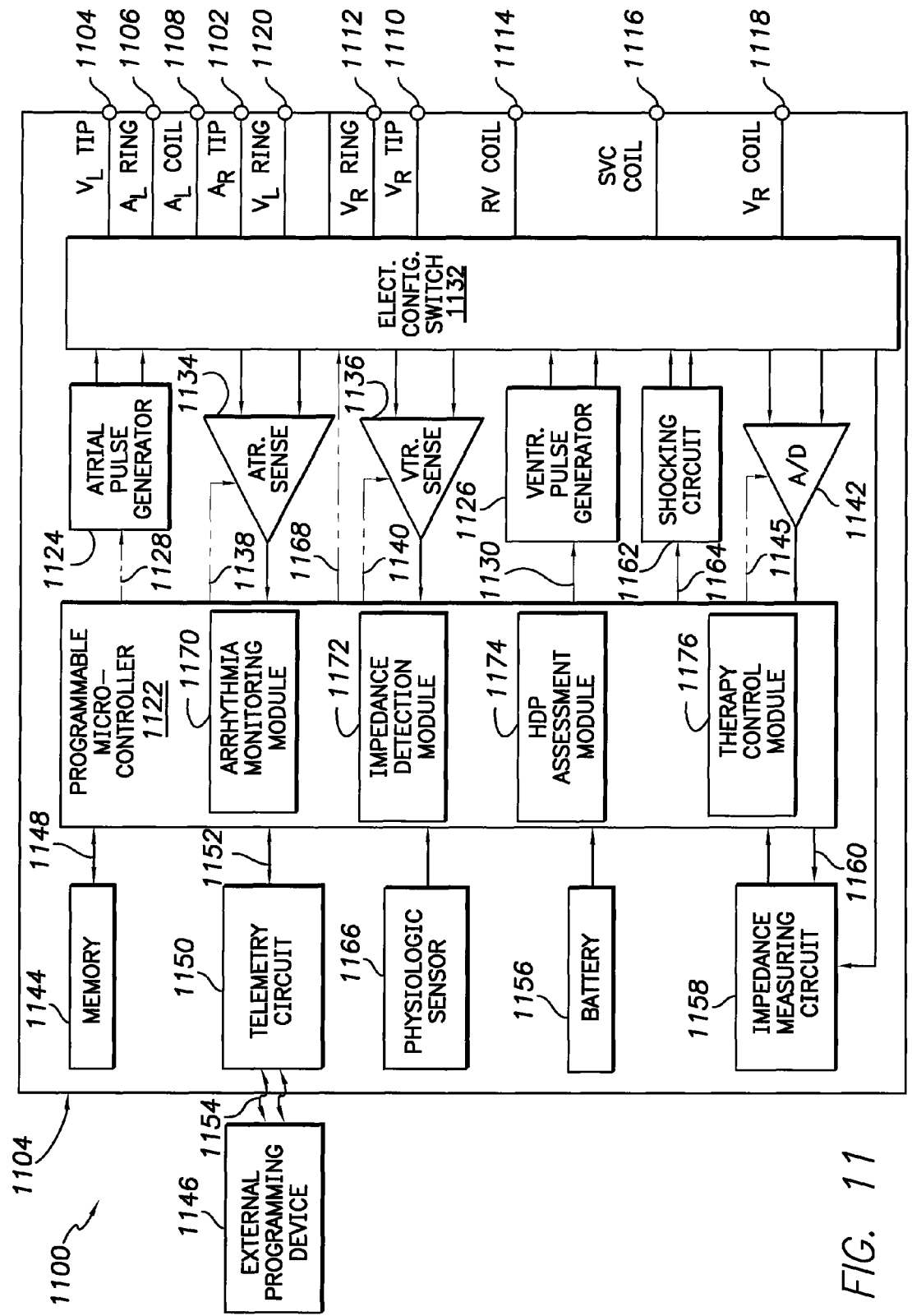
FIG. 11 illustrates a block diagram of exemplary internal components of an IMD that may be implemented in accordance with an embodiment.

FIG. 11 illustrates a block diagram of exemplary internal components of the IMD 1000. The IMD 1000 is for illustration purposes only, and it is understood that the circuitry could be duplicated, eliminated or disabled in any desired combination to provide a device capable of treating the appropriate chamber(s) of the heart with cardioversion, CRT defibrillation and/or pacing stimulation. The housing 1004 for IMD 1000 (shown schematically in FIG. 11), is often referred to as the "can", "case" or "case electrode" and may be programmably selected to act as the return electrode for all "unipolar" modes. The housing 1004 further includes a connector (not shown) having a plurality of terminals, namely a right atrial tip terminal (AR TIP) 1102, a left ventricular tip terminal (VL TIP) 1104, a left atrial ring terminal (AL RING) 1106, a left atrial shocking terminal (AL COIL) J08, a right ventricular tip terminal (VR TIP) 1110, a right ventricular ring terminal (VR RING) 1112, a right ventricular shocking terminal (RV COIL) 1114, an SVC shocking terminal (SVC COIL) 1116, a right ventricular coil terminal (VR COIL) 1118 and a left ventricular ring terminal (VL RING) 1120.

The IMD 1000 includes a programmable processor module 1122, which controls the operation of the IMD 1000 based on acquired cardiac signals and impedance vectors. The processor module 1122 (also referred to herein as a processor module or unit) typically includes a microprocessor, or equivalent control circuitry, is designed specifically for controlling the delivery of stimulation therapy and may further include RAM or ROM memory, logic and timing circuitry, state machine circuitry, and I/O circuitry. Typically, the processor module 1122 includes the ability to process or monitor input signals (e.g., data) as controlled by a program code stored in a memory. Among other things, the processor module 1122 receives, processes, and manages storage of digitized data from the various electrodes 1004, 1024-1038 (shown in FIG. 10). The processor module 1122 may also analyze the data, for example, in connection with collecting, over a period of time, variations in a segment of interest, ECI measurements and impedance vectors. For example, the processor module 1122 monitors variations in one or more of segments of interest such as the ST segment and the R-wave and variations in cardiac output and impedance vectors.

The modules in the processor module 1122 that monitor arrhythmias and CO include an arrhythmia monitoring module 1170, the impedance detection module 1172, an HDP assessment module 1174 and a therapy module 1176. The arrhythmia monitoring module 1170 determines segment variations such as ST segment variations and changes in the amplitude and rate of the R-wave. The impedance detection module 1172 measures and/or calculates one or more of the first, second and third ECI impedance vectors Z1, Z2 and Z3. The HDP assessment module 1174 monitors the CO condition based on changes in the impedance vectors monitored by the impedance detection module 1172. The therapy control module 1176 assesses and determines what therapy to deliver.

The therapy control module 1176 declaring CI based therapies, IEGM based therapies and ECI based therapies. The therapy control module 1176 over-ruling and confirming CI based therapy and non-therapy judgments utilizing ECI information.

The IMD 1000 includes an atrial pulse generator 1124 and a ventricular/impedance pulse generator 1126 to generate pacing stimulation pulses. In order to provide stimulation therapy in each of the four chambers of the heart, the atrial and ventricular pulse generators 1124 and 1126, may include dedicated, independent pulse generators, multiplexed pulse generators, or shared pulse generators. The pulse generators, 1124 and 1126, are controlled by the processor module 1122 via appropriate control signals, 1128 and 1130, respectively, to trigger or inhibit the stimulation pulses.

Switch 1132 includes a plurality of switches for connecting the desired electrodes, including the electrodes 1004 and 1024 through 1038, to the appropriate I/O circuits, thereby providing complete electrode programmability. The switch 1132, in response to a control signal 1168 from the processor module 1122, determines the polarity of stimulation pulses (e.g., unipolar, bipolar, etc.) by selectively closing the appropriate combination of switches (not shown) as is known in the art. Atrial sensing circuits 1134 and ventricular sensing circuits 1136 may also be selectively coupled to the leads 1014, 1016 and 1018 through the switch 1132 for detecting the presence of cardiac activity in each of the four chambers of the heart 1002. Control signals 1138 and 1140 from processor module 1122 direct output of the atrial and ventricular sensing circuits 1134 and 1136 that are connected to the processor module 1122. In this manner, the atrial and ventricular sensing circuits 1134 and 1136 are able to trigger or inhibit the atrial and ventricular pulse generators 1124 and 1126.

The cardiac signals are applied to the inputs of an analog-to-digital (A/D) data acquisition system 1142. The data acquisition system 1142 is configured to acquire IEGM signals, convert the raw analog data into a digital IEGM signals, and store the digital IEGM signals in a memory 1144 for later processing and/or telemetric transmission to an external device 1146.

A control signal 1145 from the processor module 1122 determines when the ND 1142 acquires signals, stores them in memory 1144, or transmits data to the external device 1146. The ND 1142 is coupled to the right atrial lead 1016 (shown in FIG. 1), the coronary sinus lead 1018 (shown in FIG. 1), and the right ventricular lead 1014 through the switch 1132 to sample cardiac signals across any combination of desired electrodes 1024-1038 (shown in FIG. 1). The processor module 1122 is coupled to the memory 1144 by a suitable data/address bus 1148, wherein the programmable operating parameters used by the processor module 1122 are stored and modified, as required, in order to customize the operation of IMD 1000 to suit the needs of a particular patient. The memory 1144 may also store data indicative of myocardial function, such as the IEGM data, ST segment shifts, reference ST segment shifts, ST segment shift thresholds, R wave amplitudes, R wave amplitude changes, impedance vectors, trend information associated with ischemic episodes, and the like for a desired period of time (e.g., 6 hours, 12 hours, 18 hours or 24 hours, and the like). The memory 1144 stores EC measurements and cardiac pacing conditions. Cardiac pacing conditions include at least one of AV delay, V-V delay, stimulation rate, stimulating electrodes chosen for actuating pacing, and stimulation lead configuration.

The operating parameters of the IMD 1000 may be non-invasively programmed into the memory 1144 through a telemetry circuit 1150 in communication with the external device 1146, such as an external device 1200 (shown in FIG. 12), a trans-telephonic transceiver or a diagnostic system analyzer. The telemetry circuit 1150 is activated by the processor module 1122 by a control signal 1152. The telemetry circuit 1150 allows intra-cardiac electrograms, and status information relating to the operation of IMD H00 (as contained in the processor module 1122 or memory 1144), to be sent to the external device 1146 through an established communication link 1154. The IMD 1000 additionally includes the battery 1156, which provides operating power to all of the circuits shown within the housing 1004, including the processor module 1122. The IMD 1000 also includes a physiologic sensor 1166 that may be used to adjust pacing stimulation rate according to the exercise state of the patient.

In the case where IMD 1000 is intended to operate as an ICD device, the IMD 1000 detects the occurrence of an arrhythmia, confirms insufficient CO and automatically applies an appropriate electrical shock therapy to the heart aimed at terminating the detected arrhythmia. To this end, the processor module 1122 further controls a shocking circuit 1162 by way of a control signal 1164. The shocking circuit 1162 generates shocking pulses of low (up to 0.5 joules), moderate (0.5-10 joules) or high energy (11 to 40 joules). Such shocking pulses are applied to the heart 1002 (shown in FIG. 10) of the patient through at least two shocking electrodes, and as shown in this embodiment, selected from the left atrial coil electrode 1028 (shown in FIG. 1), the RV coil electrode 1034 (shown in FIG. 10), and/or the SVC coil electrode 1038 (shown in FIG. 10). When the IMD operates as a pacemaker, the processor module applies a therapy using cardiac pacing conditions associated with the preferred hemodynamic performance based on the EC measurements. The processor module compares the EC measurements to determine a preferred hemodynamic performance based on the EC measurements. The processor module applies a therapy using cardiac pacing conditions associated with the preferred hemodynamic performance based on the stored EC measurements.

The IMD 1000 includes an impedance measuring circuit 1158 which is enabled by the processor module 1122 via a control signal 1160. Alternatively, the ECI impedance measuring circuit 1158 is included in the impedance detection module 1172. The ECI impedance measuring circuit 1158 is advantageously coupled to the switch 1132 so that impedance at any desired electrode may be obtained. For example, the ECI impedance measuring circuit 1158 may measure impedance vectors between predetermined combinations of the electrodes to monitor cardiac output and determine whether sufficient or insufficient CO exists.

Figure 12:
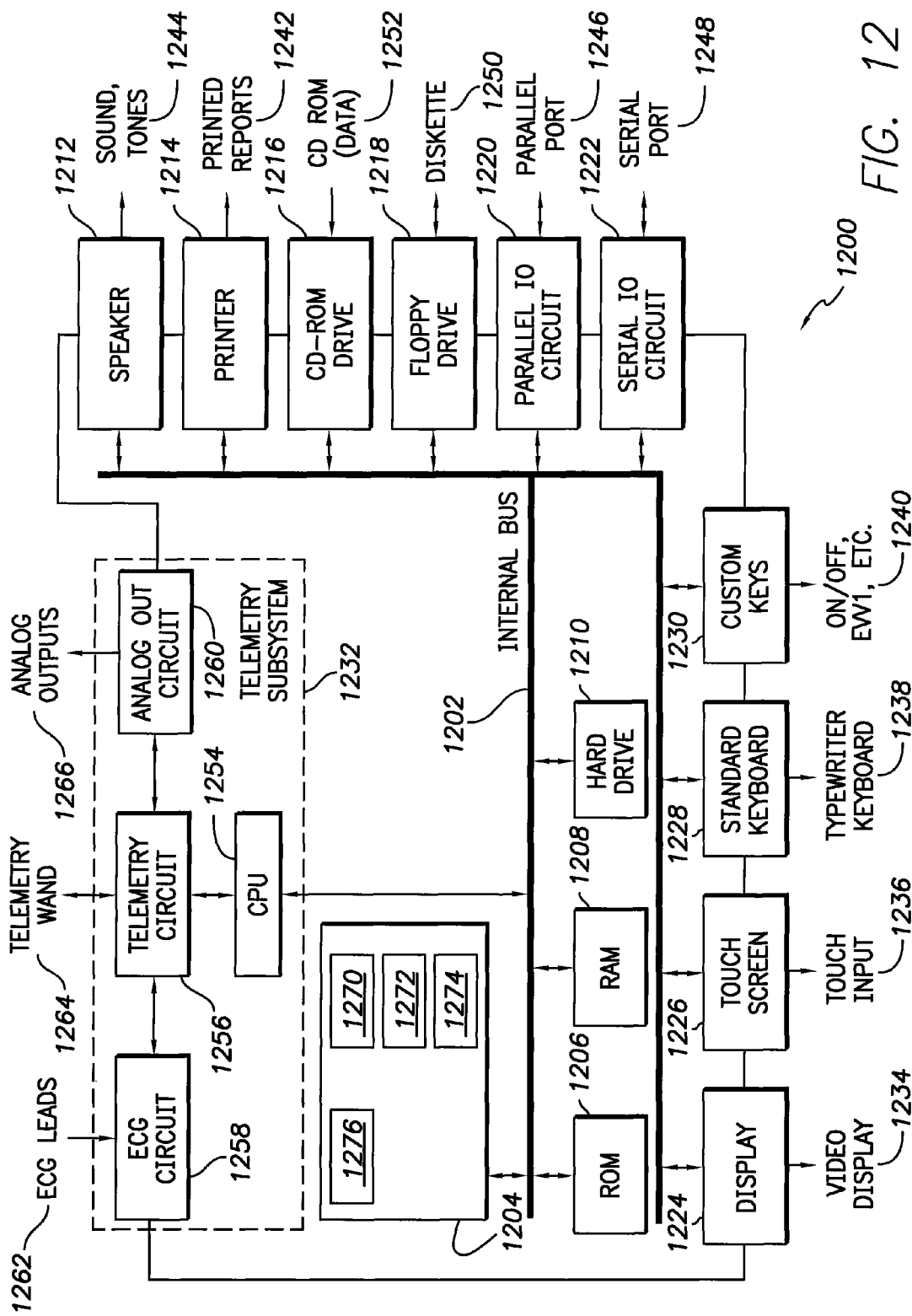
FIG. 12 illustrates a functional block diagram of an external device that may be implemented in accordance with an embodiment.

FIG. 12 illustrates a functional block diagram of the external device 1200, such as a programmer that is operated by a physician, a health care worker, or a patient to interface with IMD 1000 (shown in FIG. 10). The external device 1200 may be utilized in a hospital setting, a physician's office, or even the patient's home to communicate with the IMD 1200 to change a variety of operational parameters regarding the therapy provided by the IMD 1000 as well as to select among physiological parameters to be monitored and recorded by the IMD 1000. For example, the external device 1200 may be used to program coronary episode related parameters, such as ECI values, ECI templates, ECI thresholds, CO thresholds, and the like. Further, the external device 1200 may be utilized to interrogate the IMD 1000 to determine the condition of a patient, to adjust the physiological parameters monitored or to adapt the therapy to a more efficacious one in a non-invasive manner. Further, the external device 1100 may represent an external PSA used during implant of an IMD. The external device 1200, when used as a PSA during implant of an IMD, is in accordance with the intraoperative procedures described herein. The PSA would be connected to leads as described herein to delivery therapies. The external device 1200 may include all of the connections, switch network, sensors, generators, arrhythmia detection, ECI measurement, CO assessment and therapy delivery capabilities of an IMD such as in FIG. 11.

External device 1200 includes an internal bus 1202 that connects/interfaces with a processor module 1204, ROM 1206, RAM 1208, a hard drive 1210, a speaker 1212, a printer 1214, a CD-ROM drive 1216, a floppy drive 1218, a parallel I/O circuit 1220, a serial I/O circuit 1222, the display 1224, a touch screen 1226, a standard keyboard connection 1228, custom keys 1230, and a telemetry subsystem 1232. The internal bus 1202 is an address/data bus that transfers information (e.g., either memory data or a memory address from which data will be either stored or retrieved) between the various components described. The hard drive 1210 may store operational programs as well as data, such as reference ST segments, ST thresholds, impedance thresholds, other thresholds, timing information and the like.

The CPU 1204 typically includes a microprocessor, a micro-controller, or equivalent control circuitry, designed specifically to control interfacing with the external device 1200 and with the IMD 1000 (shown in FIG. 10). The CPU 1204 may further include RAM or ROM memory, logic and timing circuitry, state machine circuitry, and I/O circuitry to interface with the IMD. Typically, the CPU 1204 includes the ability to process or monitor input signals (e.g., data) as controlled by program code stored in memory (e.g., ROM 1206).

The modules in the processor module 1204 that monitor arrhythmias and CO include an arrhythmia monitoring module 1270, the impedance detection module 1272, an HDP assessment module 1274 and a therapy module 1276. The arrhythmia monitoring module 1270 determines segment variations such as ST segment variations and changes in the amplitude and rate of the R-wave. The impedance detection module 1272 measures and/or calculates one or more of the first, second and third ECI impedance vectors Z1, Z2 and Z3. The HDP assessment module 1274 monitors the CO condition based on changes in the impedance vectors monitored by the impedance detection module 1272. The therapy control module 1276 assesses and determines what therapy to deliver. The therapy control module 1276 declaring ICI based therapies, IEGM based therapies and ECI based therapies. The therapy control module 1276 over-ruling and confirming ICI based therapy and non-therapy judgments utilizing ECI information.

For example, the HDP assessment module 1174 may determine maximum impedance maxZ, impedance change per unit time ($\Delta Z/\Delta T$), change in cardiac output, as well as any other parameters illustrated and discusses in connection with FIGS. 3, 5, 14, 15 and 16. The HDP assessment module 1174 may determine a difference between baseline and new impedance parameters and identify whether the difference exceeds threshold limits.

The display 1224 (e.g., may be connected to a video display 1234) and the touch screen 1226 display text, alphanumeric information, data and graphic information via a series of menu choices to be selected by the user relating to the IMD 1000, such as for example, status information, operating parameters, ECI parameters, CO parameters, therapy parameters, patient status, access settings, software programming version, ST segment thresholds, impedance thresholds, CO thresholds, other thresholds, and the like. The touch screen 1226 accepts a user's touch input 1236 when selections are made. The keyboard 1228 (e.g., a typewriter keyboard 1238) allows the user to enter data to the displayed fields, operational parameters, therapy parameters, as well as interface with the telemetry subsystem 1232. Furthermore, custom keys 1230 turn on/off 1240 (e.g., EVVI) the external device 1200. The printer 1214 prints hard-copies of reports 1242 for a physician/healthcare worker to review or to be placed in a patient file, and speaker 1212 provides an audible warning (e.g., sounds and tones 1244) to the user in the event a patient has any abnormal physiological condition occur while the external device 1200 is being used. The parallel I/O circuit 1220 interfaces with a parallel port 1246. The serial I/O circuit 1222 interfaces with a serial port 1248. The floppy drive 1218 accepts diskettes 1250. The CD-ROM drive 1216 accepts CD ROMs 1252.

The telemetry subsystem 1232 includes a central processing unit (CPU) 1254 in electrical communication with a telemetry circuit 1256, which communicates with both an ECG circuit 1258 and an analog out circuit 1260. The ECG circuit 1258 is connected to ECG leads 1262. The telemetry circuit 1256 is connected to a telemetry wand 1264. The analog out circuit 1260 includes communication circuits, such as a transmitting antenna, modulation and demodulation stages (not shown), as well as transmitting and receiving stages (not shown) to communicate with analog outputs 1266. The external device 1200 may wirelessly communicate with the IMD 1000 and utilize protocols, such as Bluetooth, GSM, infrared wireless LANs, HIPERLAN, 3G, satellite, as well as circuit and packet data protocols, and the like. A wireless RF link utilizes a carrier signal that is selected to be safe for physiologic transmission through a human being and is below the frequencies associated with wireless radio frequency transmission. Alternatively, a hard-wired connection may be used to connect the external device 1200 to IMD 1000 (e.g., an electrical cable having a USB connection).

Figure 13:
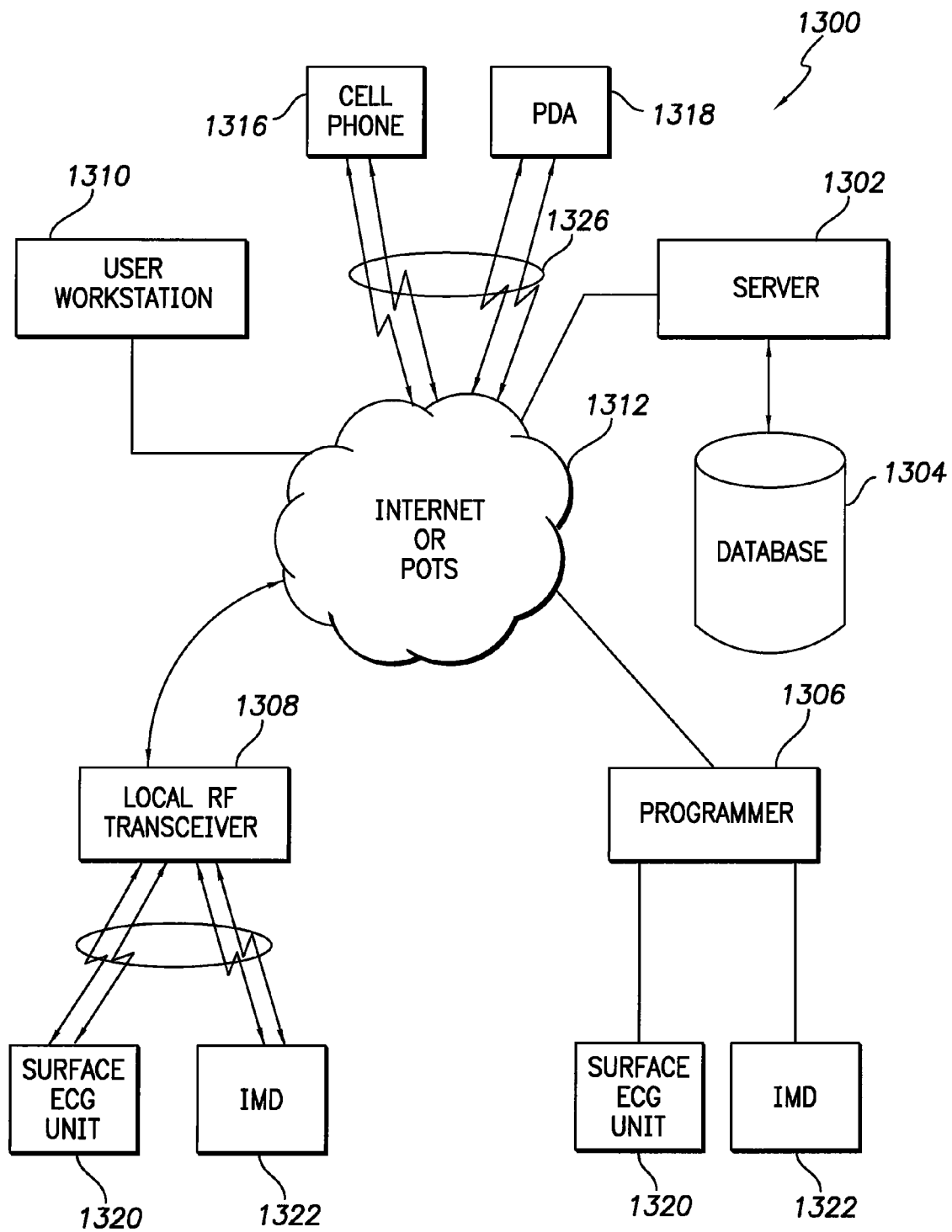
FIG. 13 illustrates a distributed processing system that may be implemented in accordance with one embodiment.

FIG. 13 illustrates a distributed processing system 1300 in accordance with one embodiment. The distributed processing system 1300 includes a server 1302 that is connected to a database 1304, a programmer 1306 (e.g., similar to external device 1200 described above and shown in FIG. 13), a local RF transceiver 1308 and a user workstation 1310 electrically connected to a communication system 1312. The communication system 1312 may be the internet, a voice over IP (VoIP) gateway, a local plain old telephone service (POTS) such as a public switched telephone network (PSTN), and the like. Alternatively, the communication system 1312 may be a local area network (LAN), a campus area network (CAN), a metropolitan area network (MAN), or a wide area network (WAM).

The server 1302 is a computer system that provides services to other computing systems (e.g., clients) over a computer network. The server 1302 acts to control the transmission and reception of information (e.g., cardiac signals, processed cardiac signals, cardiac output, ST segments, R-waves, thresholds, impedances, histograms, statistical analysis, trend lines, and the like). The server 1302 interfaces with the communication system 1312, such as the internet or a local POTS based telephone system, to transfer information between the programmer 1306, the local RF transceiver 1308, the user workstation 1310 as well as a cell phone 1316, and a personal data assistant (PDA) 1318 to the database 1304 for storage/retrieval of records of information. For instance, the server 1302 may download or upload, via a wireless connection 1326, to/from the cell phone 1316 or the PDA 1318 the results of processed cardiac signals, ST segment trends, impedance vectors, or a patient's physiological state (e.g., is the patient having or has had an ischemia) based on previously recorded cardiac information. The server 1302 may upload raw cardiac signals (e.g., unprocessed cardiac data) from a surface ECG unit 1320 or an IMD 1322 via the local RF transceiver L08 or the programmer 1306.

The database 1304 stores information such as raw cardiac data, processed cardiac signals, CO, ECI values, ECI waveforms, statistical calculations (e.g., averages, modes, standard deviations), histograms, cardiac trends (e.g., STS trends), and the like. The information is downloaded into the database 1304 via the server 1302 or, alternatively, the information is uploaded to the server from the database 1304.

The programmer 1306 is similar to the external device 1200 shown in FIG. 12 and described above, and may reside in a patient's home, a hospital, or a physician's office. Programmer 1306 interfaces with the surface ECG unit 1320 and the IMD 1322 (e.g., similar to the IMD 1000 described above and shown in FIG. 10). The programmer 1306 may wirelessly communicate with the IMD 1322 and utilize protocols, such as Bluetooth, GSM, infrared wireless LANs, HIPERLAN, 3G, satellite, as well as circuit and packet data protocols, and the like. Alternatively, a hard-wired connection may be used to connect the programmer 1306 to IMD 1000 (e.g., an electrical cable having a USB connection). The programmer 1306 is able to acquire cardiac signals from the surface of a person (e.g., ECGs), or the programmer is able to acquire intracardiac electrogram (e.g., IEGM) signals from the IMD 1322.

The local RF transceiver 1308 interfaces with the communication system 1312, to upload cardiac data, ECI measurements, CO acquired from the surface ECG unit 1320 or the IMD 1322 to the server 1302. In one embodiment, the surface ECG unit L20 and the IMD 1322 have a bi-directional connection with the local RF transceiver via a wireless connection.

The user workstation 1310 may interface with the communication system 1312 to download information via the server 1302 from the database L04. Alternatively, the user workstation 1310 may download raw data from the surface ECG unit 1320 or IMD 1322 via either the programmer 1306 or the local RF transceiver 1308. Once the user workstation 1310 has downloaded the cardiac information (e.g., raw cardiac signals, ST segments, CO, ECI measurements, impedance vectors, and the like), the user workstation 1310 may process the cardiac signals, CO, ECI measurements, create histograms, calculate statistical parameters, or determine trends and determine if the patient is suffering from insufficient CO or another physiological condition. Once the user workstation 1310 has finished performing its calculations, the user workstation 1310 may either download the results to the cell phone 1316, the PDA 1318, the local RF transceiver 1308, the programmer 1306, or to the server 1302 to be stored on the database 1304.

FIGS. 14, 15 and 16 illustrate graphs and plots of information that may be calculated by an external device or an IMD and that may be displayed to a physician on a display of an external device, such as during implantation of an IMD. The graphs and plots may also be displayed on the external device during programming or reprogramming of an implanted device.

FIG. 14 represents a series of graphs 1410, 1420, 1430 and 1440 illustrating representative relations between certain impedance features and cardiac signals. The graphs 1410, 1420, 1430 and 1440 begin at a time corresponding to the beginning of the ventricular depolarization. The graph 1410 plots a representative maximum impedance maxZ along the vertical axis relative to time along the horizontal axis. The interval 1412 illustrates the time from X0 to a minimum Z value. The graph 1410 may be analyzed such as through integration to calculate the area under the curve generally denoted as the Z area. This graph may be displayed on the external device and the Z area may be used as an indicator for a physician to determine how to set program settings for an IMD.

Graph 1420 plots an example of the unit change in impedance per unit time $\Delta Z/\Delta T$ over the same time interval along the horizontal axis. The interval 1422 illustrates the time from a start of a systole event to the end of the systolic event. Graph 1430 plots an example of ECG signal over the same time interval. Graph 1440 plots the aortic pressure AoVP and the left ventricle pressure LVP along the vertical axis over the same time period (along the horizontal axis) as graphs 1410, 1420 and 1430.

FIG. 15 illustrates data plots that may be displayed on an external device (e.g., a PSA or an external programmer) and used in connection with setting the programmable parameters of an IMD such as programming an AV delay for the IMD. The graphs 1510, 1520, X30 and 1540 illustrate time in milliseconds along the horizontal axis. The horizontal axis begins at the beginning of the AV delay and corresponds to the length of the AV delay. Graph 1510 plots the change in the maximum left ventricular $\Delta P/LT$ (millimeters of mercury per second) along the vertical axis. The data points 1512-1517 on graph 1510 represent examples of ECI information that is derived from ECI measurements and CO calculations taken during a hypothetical test of a patient. For example, the data points 1512-1517 may be obtained by placing a high fidelity pressure transducer into the left ventricle of a patient and then differentiating the pressure waveform to estimate the maximum derivative of the left ventricular pressure (maximum LV $\Delta P/\Delta T$). Left ventricular pressure may be performed at implant or at a follow-up study in a catheter lab. Each data point 1512-1517 corresponds to a different programmed AV delay. At each programmed AV delay, ECI measurements were obtained and a maximum LV $\Delta P/\Delta T$ was measured. The maximum LV $\Delta P/\Delta T$ is based upon a baseline measurement. As shown in graph 1510, at point 1516 (an AV delay of approximately 120 milliseconds), the maximum left ventricular change in pressure per unit time reached a maximum point.

With reference to graph 1520, the change in cardiac output is plotted in milliliters per minute along the vertical axis. The zero value along the vertical axis corresponds to a baseline cardiac output measurement. Data points 1521-1526 correspond to examples of potentially measured changes in cardiac output in milliliters per minute at each programmed AV delay. For example, the data point at 1522 indicates that the change in cardiac output from a baseline cardiac output value does not change very much when the AV delay is approximately 50 milliseconds. Similarly, data point 1523 indicates that when the AV delay is at approximately 75 milliseconds, the change in cardiac output remains close to the baseline cardiac output. However, when the AV delay is increased to approximately 120 milliseconds, the cardiac output increases significantly to approximately 140 milliliters per minute.

By adjusting the AV delay parameter during implant of a new IMD or during reprogramming of an existing IMD while simultaneously obtaining ECI measurements to calculate cardiac output, data such as illustrated in the exemplary graph 1520 can be obtained to determine a preferred AV delay program value. In this case, cardiac output can be estimated by taking the product of $\Delta Z$ times the mechanical heart rate with a proportionality factor that is in the range of 10 to 100 ml/ohm/bpm.

Graph 1530 plots the time between the start of a ventricular depolarization to the end of systole along the vertical axis and the length of the programmed AV delay value along the horizontal axis. When the AV delay is programmed to be 25 or 50 milliseconds, the interval between Q and the end ejection time is quite small. However, when the AV delay is increased to roughly 120 milliseconds, the time between Q and the end of systole increases to a maximum of approximately 24 milliseconds.

Graph 1540 illustrates an exemplary plot of the change in Z area (in ohm seconds) as the AV delay is programmed to different values. When the AV delay is programmed to roughly 120 milliseconds, the change in Z area reaches a local maximum of slightly less than 0.02 ohm seconds.

FIG. 16 illustrates an exemplary plot of the maximum change in impedance max$\Delta$Z (along the vertical axis) relative to the systolic blood pressure (along the horizontal axis). Data points 1611-1616 show a relatively linear relation between the change in systolic blood pressure and the maximum change in impedance.

Figure 17:
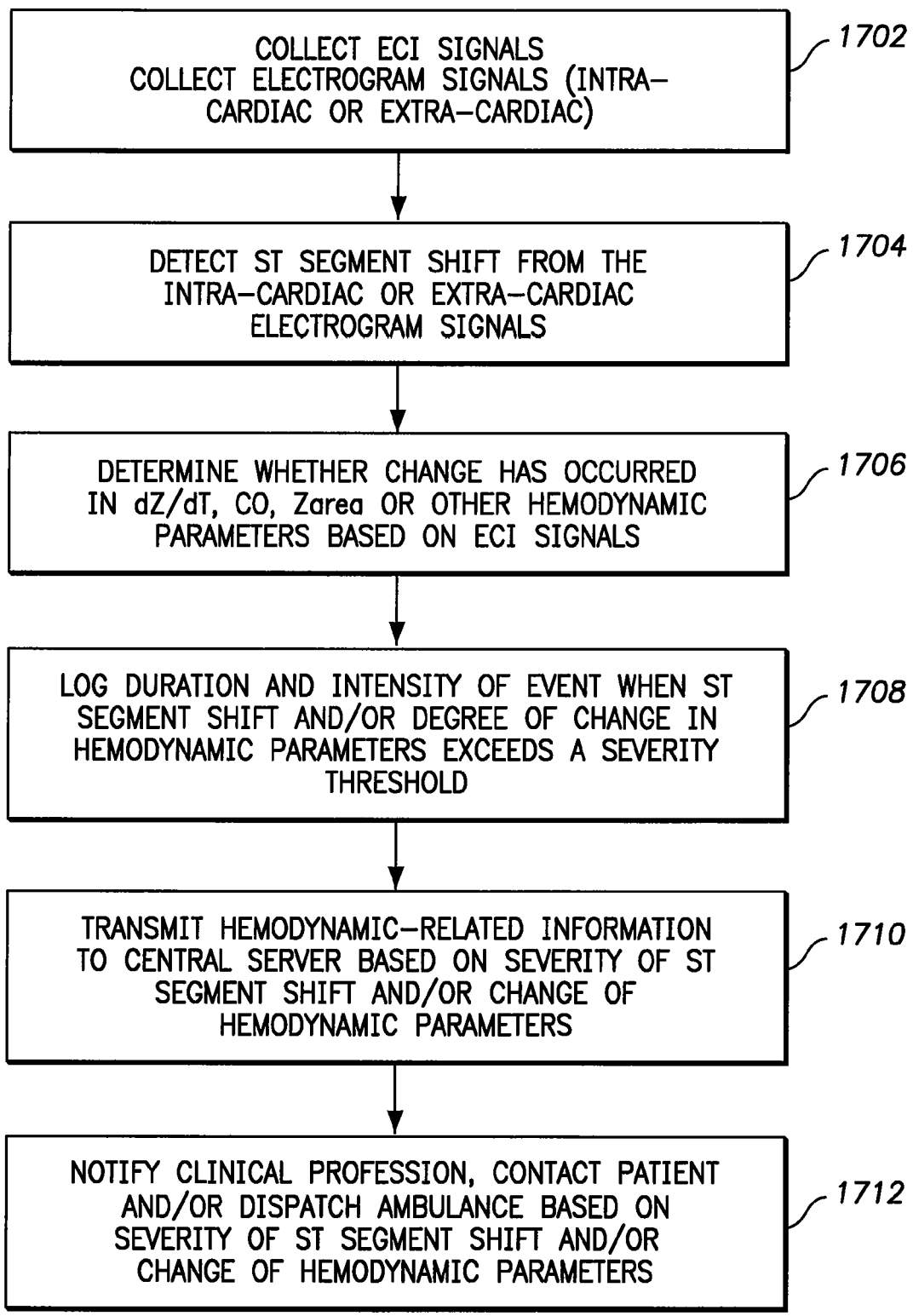
FIG. 17 illustrates another embodiment in which the ECI signal may be used to detect and confirm hemodynamically compromised ischemia.

FIG. 17 illustrates another embodiment in which the ECI signal may be used to detect and confirm hemodynamically compromised ischemia. Ischemia may be deemed as tolerated or poorly tolerated. Typically the ischemic episode may initially trigger an increase in heart rate with a concomitant decrease in stroke volume and contractility. It is of greater concern when ischemia occurs in conjunction with a change in cardiac hemodynamic function. When in this mode of detection and confirmation, the device would operate as follows. Beginning at 1702, the IMD collects ECI signals and electrogram signals. The electrogram signals may be collected from intra-cardiac electrodes or from extra-cardiac electrodes. Optionally, the electrogram signals may be collected from external EKG electrodes. The arrhythmia monitoring module detects (at 1704) an ST segment shift from electrogram signals. The device analyzes the ECI signals (at 1706) to check for a change in dZ/dT, cardiac output, Z-area and the like. The device records the degree of change in dZ/dT, cardiac output, Z-area or in other hemodynamic-related information. The amount of shift in the ST segment is also referred to as the severity of the ST segment shift. The amount of change in the dZ/dT, cardiac output, Z-area represents a degree of hemodynamic compromise. At 1708, it is determined whether the amount of ST segment shift exceeds an ST segment shift severity threshold.

At 1708, it is also determined whether the change in the dZ/dT, cardiac output, or Z-area exceeds a hemodynamic compromise severity threshold. When the ST segment shift and/or hemodynamic compromise severity threshold are exceeded, the duration and intensity of the event may simply be logged for later review and used to compute an ischemic burden. If the event exceeds one or both severity thresholds at 1710, the event may trigger an automatic transmission from the IMD of the information to a central server. By way of example only, the information transmitted may include the heart rate, ST segment shift, the total and/or change in dZ/dT, the total and/or change in cardiac output, the total and/or change in Z-area and the like. By way of example, the transmission of information from the IMD may be to an external programmer, a portable Holter-type monitor, or through the equipment and devices illustrated in FIG. 13. The central server, network, IMD and/or an external programmer may also alert clinical professionals of the critical nature of the patient's ischemia and hemodynamic compromise. The alert may include information collected by the IMD, as well as relative analysis of the information. For example, the clinical professional may be presented with the data and graphs in FIGS. 3, 5 and 14-16. The clinical professional may also be presented with a relative evaluation of the degree of hemodynamic compromise, such as a percentage of baseline hemodynamic performance (e.g., 70% of baseline CO).

The process of FIG. 17 enables prompt delivery of medical attention to mitigate the patient's clinical danger. For example, at 1712 when severe hemodynamic compromise is detected, hemodynamic-related information may be conveyed to a central server (FIG. 13). The server may then notify a clinician who may contact the patient to check on the patient's condition. The clinician may dispatch an ambulance to the patient. The server may automatically dispatch an ambulance to the location of the patient without waiting for input from the clinician.

It is to be understood that the above description is intended to be illustrative, and not restrictive. For example, the above-described embodiments (and/or aspects thereof) may be used in combination with each other. In addition, many modifications may be made to adapt a particular situation or material to the teachings of the invention without departing from its scope. While the dimensions, types of materials and coatings described herein are intended to define the parameters of the invention, they are by no means limiting and are exemplary embodiments. Many other embodiments will be apparent to those of skill in the art upon reviewing the above description. The scope of the invention should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, the terms "first," "second," and "third," etc. are used merely as labels, and are not intended to impose numerical requirements on their objects. Further, the limitations of the following claims are not written in means—plus-function format and are not intended to be interpreted based on 35U.S.C. §112, sixth paragraph, unless and until such claim limitations expressly use the phrase "means for" followed by a statement of function void of further structure.

What is claimed is:

1. A medical device comprising:
   a lead assembly configured to be at least partially located proximate to the heart, the lead assembly including an extra-cardiac (EC) electrode to be positioned proximate to at least one of a superior vena cava (SVC) and a left ventricle (LV) of a heart, the lead assembly including a subcutaneous remote-cardiac (RC) electrode configured to be located remote from the heart such that at least a portion of the greater vessels are interposed between the RC electrode and the EC electrode to establish an extra-cardiac impedance (ECI) vector, and
   a processor module to measure extra-cardiac impedance along the ECI vector to obtain ECI measurements, the processor module assessing a hemodynamic performance assessment based on the ECI measurements.

2. The device of claim 1, wherein further comprising memory to store the EC measurements and associated cardiac pacing conditions including at least one of AV delay, V-V delay, stimulation rate, stimulating electrodes chosen for actuating pacing, and stimulation lead configuration.

3. The device of claim 1, wherein the processor module compares the EC measurements to determine a preferred hemodynamic performance based on the EC measurements, the processor module applies a therapy using cardiac pacing conditions associated with the preferred hemodynamic performance based on the stored EC measurements.

4. The device of claim 1, wherein the EC electrode is located outside of the heart and in the SVC and wherein the RC electrode is located in a left subclavian pocket of the patient.

5. The device of claim 1, wherein the lead assembly forms a bipolar impedance configuration that measures impedance between the EC and RC electrodes.

6. The device of claim 1, wherein the ECI vector passes through at least a portion of at least one of pulmonary arteries, pulmonary veins, brachiocephalic arteries and brachiocephalic veins, left carotid artery and left subclavian artery.

7. The device of claim 1, wherein the greater vessels comprise pulmonary arteries, pulmonary veins, brachiocephalic arteries and brachiocephalic veins, left carotid artery and left subclavian artery.

8. The device of claim 1, the processor module to analyze parameters of the ECI measurements for current ECI values relative to ECI thresholds to determine whether sufficient hemodynamic performance exists, wherein hemodynamic performance is comprised of at least one of cardiac output, systolic blood pressure, diastolic blood pressure, contractility, stroke volume, systolic time, and Q-wave to onset of systole, QRS to onset of systole.

9. The device of claim 1, the processor module to obtain baseline ECI values from a baseline ECI measurement when normal hemodynamic performance is present, the processor module utilizing the baseline ECI values to analyze new ECI measurements to determine whether sufficient hemodynamic performance exists.

10. The device of claim 1, further comprising memory to store ECI pattern templates, the processor module to correlate the ECI pattern templates to new ECI measurements to determine whether sufficient hemodynamic performance exists.

11. The device of claim 1, the processor module to determine whether to apply a corrective therapy based on the ECI measurements.

12. The device of claim 1, further comprising cardiac electrodes to collect IEGM signals, the processor module to analyze the IEGM signals utilizing an arrhythmia detection algorithm, the processor module declaring an IEGM based therapy when an arrhythmia episode is identified based on the IEGM signals, the processor module suspending the IEGM based therapy when the ECI measurements indicate that sufficient hemodynamic performance exists.

13. The device of claim 1, further comprising cardiac electrodes to collect IEGM signals, the processor module to analyze the IEGM signals utilizing an arrhythmia detection algorithm, the processor module declares a non-therapy judgment when a rhythm episode is identified based on the IEGM signals, the processor module over-ruling the non-therapy judgment and declaring an ECI based therapy when the ECI measurements indicate that insufficient hemodynamic performance exists.

14. A method for assessing hemodynamic stability, comprising:
providing a lead assembly configured to be at least partially located proximate to the heart, the lead assembly including an extra-cardiac (EC) electrode to be positioned proximate to at least one of a superior vena cava (SVC) and a left ventricle (LV) of a heart, the lead assembly including a subcutaneous remote-cardiac (RC) electrode configured to be located remote from the heart such that at least a portion of the greater vessels are interposed between the RC electrode and the EC electrode to establish an extra-cardiac impedance (ECI) vector;
measuring extra-cardiac impedance along the ECI vector to obtain ECI measurements;
assessing hemodynamic performance based on the ECI measurements.

15. The method of claim 14, further comprising locating the EC electrode is outside of the heart and in the SVC and locating the RC electrode in a left subclavical pocket of the patient.

16. The method of claim 14, further comprising forming a bipolar impedance configuration that measures impedance between the EC and RC electrodes.

17. The method of claim 14, further comprising configuring the ECI vector to pass through at least a portion of at least one of pulmonary arteries, pulmonary veins, brachiocephalic arteries and brachiocephalic veins, left carotid artery and left subclavian artery.

18. The method of claim 14, further comprising analyzing parameters of the ECI measurements for current ECI values relative to ECI thresholds to determine whether sufficient cardiac output exists.

19. The method of claim 14, further comprising obtaining baseline ECI values from a baseline ECI measurement when normal hemodynamic performance is present; and utilizing the baseline ECI values to analyze new ECI measurements to determine whether sufficient hemodynamic performance exists.

20. The method of claim 14, further comprising determining whether to apply a corrective therapy based on the ECI measurements.

* * * * *